US007425437B2

(12) United States Patent
UytdeHaag et al.

(10) Patent No.: US 7,425,437 B2
(45) Date of Patent: Sep. 16, 2008

(54) VACCINES AGAINST WEST NILE VIRUS

(75) Inventors: Alphonsus G. C. M. UytdeHaag, Vleuten (NL); Govert Johan Schouten, Leiderdorp (NL); Jaap Goudsmit, Amsterdam (NL)

(73) Assignee: Crucell Holland B.V., Leiden (NL)

( * ) Notice: Subject to any disclaimer, the term of this patent is extended or adjusted under 35 U.S.C. 154(b) by 230 days.

(21) Appl. No.: 11/110,517

(22) Filed: Apr. 20, 2005

(65) Prior Publication Data

US 2005/0186222 A1  Aug. 25, 2005
US 2008/0206279 A9  Aug. 28, 2008

Related U.S. Application Data

(63) Continuation of application No. PCT/EP2003/05080, filed on Nov. 7, 2003, which is a continuation-in-part of application No. PCT/EP03/50129, filed on Apr. 28, 2003, and a continuation-in-part of application No. PCT/NL02/00718, filed on Nov. 8, 2002, and a continuation-in-part of application No. 09/722,867, filed on Nov. 27, 2000, now abandoned, which is a continuation-in-part of application No. 09/449,854, filed on Nov. 26, 1999, now Pat. No. 7,192,759.

(51) Int. Cl.
C12N 7/00 (2006.01)
C12N 7/02 (2006.01)
C12N 7/06 (2006.01)

(52) U.S. Cl. .................... 435/235.1; 435/238; 435/239

(58) Field of Classification Search .............. 424/204.1, 424/218.1, 199.1, 93.2; 435/5, 6, 456
See application file for complete search history.

(56) References Cited

U.S. PATENT DOCUMENTS

| 5,494,671 | A | 2/1996 | Lai et al. |
| 5,514,375 | A | 5/1996 | Paoletti et al. |
| 5,744,140 | A | 4/1998 | Paoletti et al. |
| 5,744,141 | A | 4/1998 | Paoletti et al. |
| 6,184,024 | B1 | 2/2001 | Lai et al. |
| 6,258,788 | B1 | 7/2001 | Schmaljohn |
| 6,306,899 | B1 | 10/2001 | Cheng et al. |
| 6,416,763 | B1 | 7/2002 | McDonel et al. |
| 6,432,411 | B1 | 8/2002 | Ivy et al. |
| 6,455,509 | B1 * | 9/2002 | Kochel et al. .................. 514/44 |
| 6,685,948 | B1 * | 2/2004 | Zeng et al. ............... 424/218.1 |

FOREIGN PATENT DOCUMENTS

| EP | 0 102 228 A | 3/1984 |
| EP | 0 691 404 A | 1/1996 |
| EP | 0 869 184 A | 10/1998 |
| EP | 0 872 553 A | 10/1998 |
| WO | WO 98/37911 | 9/1998 |
| WO | WO 99/26653 | 6/1999 |
| WO | WO 99/63095 | 12/1999 |
| WO | WO 00/10991 | 3/2000 |
| WO | WO 00/12128 | 3/2000 |
| WO | WO 00/14245 | 3/2000 |
| WO | WO 2000 063403 | * 10/2000 |
| WO | WO 01/03729 | 1/2001 |
| WO | WO 01/38362 | 5/2001 |
| WO | WO 01/39802 | 6/2001 |
| WO | WO 01/60315 | 8/2001 |
| WO | WO 01/60847 | 8/2001 |
| WO | WO 02/15664 | 2/2002 |

OTHER PUBLICATIONS

Leible et al., "Adjuvant/carrier activity of inactivated tick-borne encephalitis virus," Vaccine, vol. 16, No. 4, pp. 340-345 (1998).*
Fields et al., Virology (Third Ed.), excerpt, pp. 931-932 (1996).*
Pau et al, "The human cell line PER.C6 provides a new manufacturing system for the production of influenza vaccines," Vaccine 19 (2001), pp. 2716-2721.*
PCT International Preliminary Examination Report, PCT/EP2003/50806, dated Feb. 17, 2005.
PCT International Search Report, PCT/EP2003/50806, dated Apr. 26, 2004.
Shi et al., "Infectious cDNA Clone of the Epidemic West Nile Virus from New York City," *J. of Virology*, Jun. 2002, pp. 5847-5856, vol. 76, No. 12.
Yamschihikov et al., "An Infectious Clone of the West Nile Flavivirus," Virology, Mar. 15, 2001, pp. 294-304, vol. 281, No. 2.
Malkinson et al, "Use of Live and Inactivated Vaccines in the Control of West Nile Virus in Domestic Geese," Annals of the New York Academy of Sciences, 2001, pp. 255-261.
Shen et al., "Early Induction of Interferon-Independent Virus-Specific ICAM-1 (CD54) Expression by Flavivirus in Quiescent but not Proliferating Fibroblasts—Implications for Virus—Host Interactions," Virology, 1995, pp. 437-449, vol. 208, No. 2.
Boa et al., "Flavivrus Induces MHC Antigen on Human Myoblasts: A Model of Autoimmune Myositis?" Muscle and Nerve, Nov. 1992, pp. 1271-1277, vol. 15, No. 11.

(Continued)

*Primary Examiner*—Mary E Mosher
(74) *Attorney, Agent, or Firm*—TraskBritt

(57) ABSTRACT

The present invention relates to novel vaccines containing (whole-inactivated) West Nile Viruses and/or West Nile viral proteins derived therefrom, produced on human cells, wherein the human cells comprise a sequence encoding at least one early region-1 (E1) gene product of an adenovirus. The cells are preferably cultured in suspension to very high densities and under serum-free conditions. Herein, it is disclosed that use of such cells results in high titers of West Nile Virus produced.

17 Claims, 14 Drawing Sheets

OTHER PUBLICATIONS

Gallimore et al., Transformation of Human Embyro Rotinoblasts with Simian Virus 40, Adenovirus and ras Oncogenes, Anticancer Research, May 3, 1986, pp. 499-508, vol. 6, No. 3.

Jia et al., "Genetic analysis of West Nile Virus New York 1999 encephalitis virus," The Lancet, Dec. 4, 1999, pp. 1971-1972, vol. 354, No. 9196.

Bae et al., "Production of Hantaan Virus from Human Immortalized Retina Cell and Its Immmogenicity," J. Microbiol. Biotechnol., Dec. 20, 2002, pp. 882-889, vol. 12, No. 6.

* cited by examiner

FIG. 2

FIG. 3

Phylogenetic Tree of West Nile Viruses based on the Envelope sequences

Lineage 1 associated with severe disease:
Romania 1996 H, Romania 1996, South Africa, Israel 1952, Egypt 1951, France 1965, Senegal 1979, Algeria 1968, New York 1999, Israel 1998, C.Afr.Rep. 1989, Italy 1998, Morocco 1996, Romania 1996, Kenya 1998, Senegal 1993, IvoryCoast 1981, Kunjin 1994, Kunjin 1966, Kunjin 1973, Kunjin 1960, Kunjin 1984b, Kunjin 1984a, Kunjin 1991, India 1955, India 1955, India 1980, India 1958

Lineage 2 associated with mild disease:
Madagascar 1978, Madagascar 1988, Kenya, Madagascar 1986, Uganda 1959, C.Afr.Rep. 1972a, C.Afr.Rep. 1983, C.Afr.Rep. 1972b, Nigeria, Uganda, Senegal 1990, JE SA 14 distance 0.045

MEGA, distance tree, Kimura 2-parameter, neighbor-joining

FIG. 5

VACCINES AGAINST WEST NILE VIRUS

CROSS-REFERENCE TO RELATED APPLICATION

This application is a continuation of PCT International Patent Application No. PCT/EP2003/050806, filed on Nov. 7, 2003, designating the United States of America, and published, in English, as PCT International Publication No. WO 2004/042042 A1 on May 21, 2004, which application is a continuation-in-part of PCT International Patent Application No. PCT/NL02/00718, filed Nov. 8, 2002, and a continuation-in-part of PCT International Patent Application No. PCT/EP03/50129, filed Apr. 28, 2003, the contents of the entirety of each are incorporated herein by this reference. This application is also a continuation-in-part of U.S. patent application Ser. No. 09/722,867 filed on Nov. 27, 2000 now abandoned which is a continuation-in-part of U.S. patent application Ser. No. 09/449,854, now U.S. Pat. No. 7,192,759, filed on Nov. 26, 1999.

TECHNICAL FIELD

The invention relates to the field of medicine. In particular, it relates to vaccines against flaviviruses and, more specifically, to West Nile Virus and to methods of producing the same.

BACKGROUND

The Flaviviridae family contains three genera: the flaviviruses, the pestiviruses and the Hepatitis C viruses. Flaviviruses are small spherical enveloped viruses with virions composed of three structural proteins designated C, M and E, and a single (+)RNA genome of approximately 11,000 nucleotides (Chambers et al. 1990; Brinton 2002). The flavivirus genus comprises more than 60 highly related viruses including several human pathogens of global and local epidemiological importance, with most of them being transmitted by arthropod vectors. With a combined toll of hundreds of millions of infections around the world annually, yellow fever virus, Japanese encephalitis virus, St. Louis encephalitis virus, Murray Valley encephalitis virus, tick-borne encephalitis virus, dengue virus, and West Nile Virus continue to be in the focus of epidemiological surveillance worldwide. While the availability of an efficient vaccine and control of mosquito vectors have resulted in significant improvement of the epidemiological situation in yellow fever, other existing, as well as emerging, flavivirus-associated diseases for which vaccines are not yet available continue to challenge experimental virology. West Nile Virus was first identified in 1937 in the West Nile district in Uganda (Smithburn et al. 1940) and has now been recognized as the most widespread of the flaviviruses, with a geographic distribution in Africa, Asia, Europe, Australia and North America (Campbell et al. 2002). Recent outbreaks have been reported in Russia, Israel, Romania, and the United States (Hubalek and Halouzka 1999; Anderson et al. 1999; Jia et al. 1999; Lanciotti et al. 1999), with over 3000 individuals tested positive and nearly 300 people killed. The virus was found to have caused infections in persons in over 40 different states in the United States. Symptoms vary from fever, headache, skin rash, swollen lymph glands, neck stiffness, stupor, disorientation, tremors, convulsions, muscle weakness, pancreatitis, myocarditis, and paralysis to coma, while in 15% of the cases, the disease progresses to a more severe state (e.g., West Nile encephalitis), which can lead to death. Besides infecting humans, West Nile Viruses are also known to infect horses and several bird species and cause severe illness and death. The outbreak in New York in 1999 started with massive death among crows and several lethal cases in horses.

Several approaches were followed in the art to counteract the infection and resulting illnesses brought about by flaviviruses. One proposed approach was to treat individuals with chemical compounds, such as ribavirin and nucleoside analogues, and biologicals such as interferon alpha-2b and/or helioxanthin (WO 00/10991; WO 02/15664; and U.S. Pat. No. 6,306,899). Others have focused on the development of vaccines containing: chimeric flaviviruses, (manipulated) yellow fever viruses for cross-vaccination, subviral particles, replication-defective flaviviruses, (naked) nucleic acid, recombinant subunits (envelope proteins), or poxviruses containing flavivirus antigens (Arroyo et al. 2001; Wang et al. 2001; Chang et al. 2001; WO 00/12128; WO 01/03729; WO 02/72036; WO 99/26653; WO 99/63095; WO 01/60315; WO 02/68637; EP 0869184 A; WO 00/14245; WO 02/74963 EP 0691404 A WO 98/37911; WO 01/39802; WO 01/60847; EP 0102228 A; EP 0872553 A; and U.S. Pat. Nos. 6,184,024, 5,514,375, 5,744,140, 5,744,141 6,416,763, 6,432,411, 5,494,671, and 6,258,788). One veterinary vaccine containing inactivated West Nile Viruses was approved in August 2001, solely for use in horses. In Israel, an approach was taken to produce a West Nile Virus strain, isolated from geese (Goose Israel 1998), in mouse brains, to inactivate it by formaldehyde and to apply the vaccine in geese flocks (Malkinson et al. 2001). This veterinary vaccine (for use in geese flocks) was approved by the Israeli authorities in July/August 2001. Numerous disadvantages exist with the treatments and vaccines mentioned above related to dosages, ineffectiveness, required titers in production, and side effects (Monath et al. 2001). Disadvantages in the production of vaccines on systems such as mouse brains are clearly related to safety, animal welfare, adverse side effects, allergic properties, titers and scalability. No human vaccines have been produced to date. To elicit a proper immune response against the wild-type virus, it would be clearly desirable to have a vaccine comprising a virus that contains most, if not all, of its antigenic proteinaceous molecules in its wild-type configuration, but that does not replicate and that is able to elicit a significant immune response, resulting in a proper protection against subsequent infections. Such vaccines should preferably contain whole-inactivated viruses. However, safe and large-scale production methods to obtain such whole-inactivated viruses are not available in the art for vaccines directed against West Nile Virus. A cell-based system based on the use of animal cells, such as Vero cells, has disadvantages since Vero cells are normally grown on microcarriers and, therefore, highly suited for large-scale production and the culture is, by definition, not free from animal-derived components. It is an object of the present invention to provide novel methods for producing West Nile Virus, preferably on a large scale, for the production of novel vaccines based on West Nile Virus particles.

SUMMARY OF THE INVENTION

The present invention relates to methods for producing a West Nile Virus comprising the steps of:

either infecting a cell, or a culture of cells, with a West Nile Virus, or providing a cell or a cell culture, with nucleic acid coding for the West Nile Virus; and culturing the cell, or the culture of cells, obtained in either one of the previous steps in a suitable medium under conditions that cause or allow the virus to replicate in the cell or that cause or allow expression of the nucleic acid coding for the West Nile Virus or the culture of cells, thereby causing the West Nile Virus to be produced, wherein the cell or the culture of cells is characterized in that it expresses at least an E1A protein of an adenovirus.

Products obtainable by the methods of the invention are also part of the invention and may be used for vaccines in veterinary and human applications. The invention thus also provides methods for producing, inactivating and disrupting West Nile Viruses to be used in veterinary applications.

The invention further relates to West Nile Viruses or West Nile viral proteins for use in a vaccine obtainable by a method or a use according to the invention, the West Nile Virus or the West Nile viral protein being free of any non-human mammalian proteinaceous material. Such West Nile Viruses and/or West Nile viral proteins are suitable for the production of human and/or veterinary vaccines against flavivirus infections, such as infections by West Nile Virus, but also to viruses highly related to West Nile Virus. The invention also relates to such vaccines. Moreover, the invention relates to human cells having a sequence encoding at least one E1 gene product of an adenovirus in its genome and having a nucleic acid encoding a West Nile Virus or at least one West Nile viral protein.

The invention also relates to the production of a lineage II strain of West Nile Virus that can be used in a vaccine which can subsequently be applied for protection against a lineage I strain infection, via a mechanism referred to as cross-protection.

BRIEF DESCRIPTION OF THE DRAWINGS

FIG. 2 shows the immune fluorescent staining of cells as deposited under ECACC no. 96022940 infected with West Nile Virus using a human serum as a negative control and a serum derived from a monkey that was infected with yellow fever virus.

FIG. 3 is a phylogenetic tree of a large set of West Nile Viruses based on sequences of the envelope protein. In the upper part, the lineage I strains are given (generally associated with severe disease) and in the lower part, the lineage II strains are given (generally associated with mild disease).

FIG. 5 is a diagram showing the titer of the virus preparation produced on cells as deposited under ECACC no. 96022940 and in Mouse Brain. The titration was determined using suckling mice and given in MLD50/0.1 ml.

DETAILED DESCRIPTION OF THE INVENTION

Figure 1:
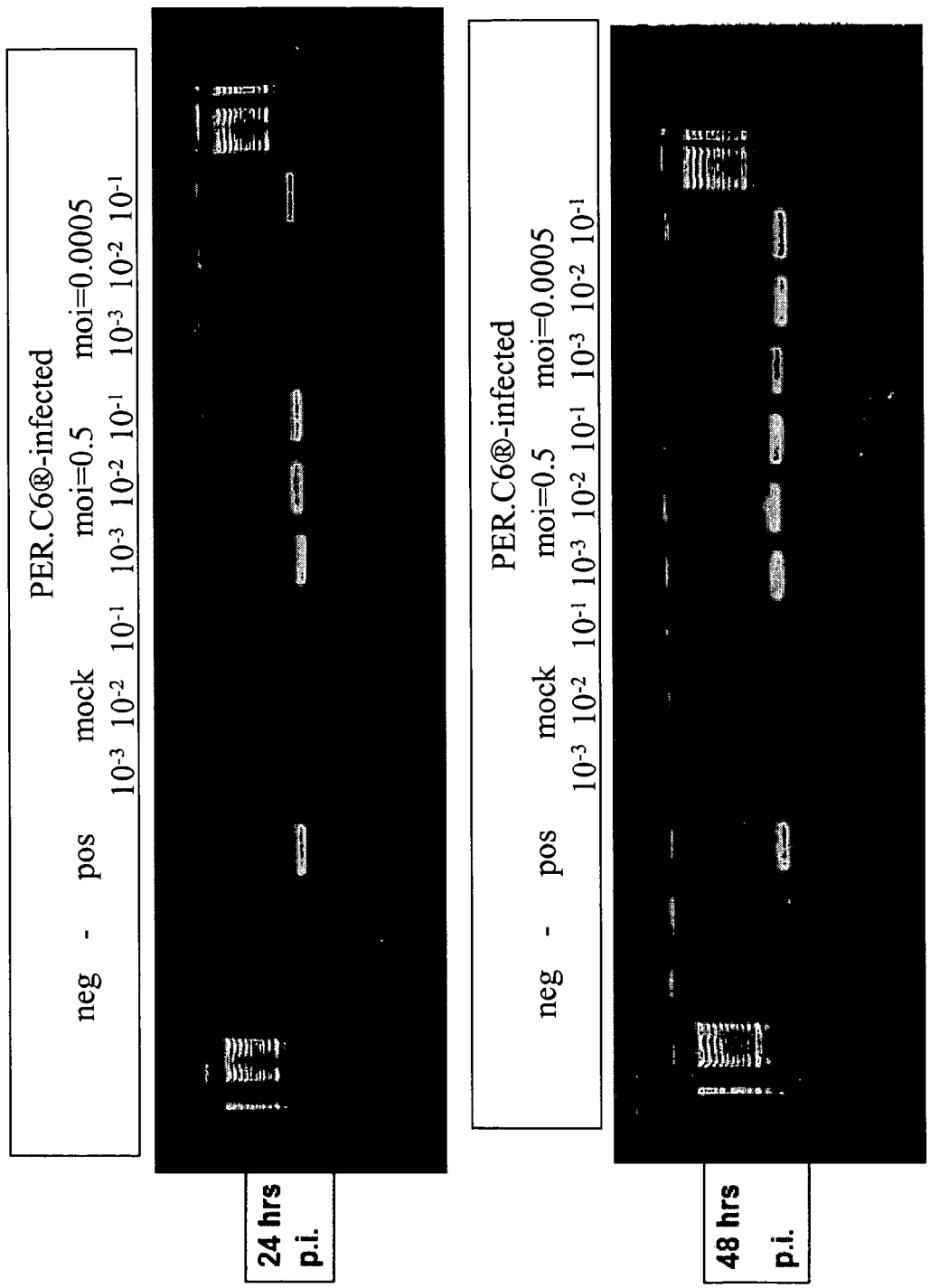
FIG. 1 shows the Reverse Transcriptase PCR (RT-PCR) products using samples of cells as deposited under ECACC no. 96022940 infected with West Nile Virus.

The present invention relates to new vaccines against West Nile Virus and to methods of producing the same. It is appreciated in the art that there is a great need for a potent vaccine against West Nile Virus that should be sufficiently protective and that could be produced in a large scale. The invention relates to the production of a whole-inactivated (or killed) virus, based on West Nile Virus. More specifically, it relates to a whole-inactivated West Nile Virus that is being produced using cells that grow in suspension and under serum-free conditions (animal component free) to enable one to produce large-scale batches. It further relates to the down-stream processes for inactivating and purifying the produced viruses and to the compositions for prophylactic and therapeutic treatment.

In the art, West Nile Viruses have been grown and passaged on a limited number of cells: Baby Hamster Kidney (BHK) cells, fibroblasts, monkey kidney cells (Vero), murine macrophages, C6/36 cells, and HeLa cells (Dunster et al. 1990; Kurane et al. 1992; Wengler et al. 1990). Moreover, West Nile Virus has also been produced on infant mouse brains. None of these systems is highly suitable for producing West Nile Viruses in a combination of large-scale production, in suspension and under animal component-free and/or serum-free conditions. These procedures are not especially suited for the production of vaccines that are to be used in humans. Vero cells grow on microcarriers, not in suspension, while HeLa cells are aggressive tumor cells. BHK cells are not generally found to be safe for the production of therapeutics. The other systems do not provide a platform for large-scale production since cells need to grow indefinitely and should not be derived from a tumor. Also, vaccines produced on mouse brains are not desired due to safety, animal welfare, possible adverse side effects, allergic reactions and scalability. Importantly, an embryonic human retinoblast cell line obtained by transformation and immortalization through the early region-1 (E1) from Adenovirus serotype 5 (cells as deposited under ECACC no. 96022940), a cell-based platform technology marketed by Crucell Holland B.V. under the trade name PER.C6®, has been described to support the growth of influenza virus, measles virus and Herpes simplex virus type 1 and 2 (WO 01/38362, incorporated in its entirety by reference herein). Although the use of cells as deposited under ECACC no. 96022940 for the production of flaviviruses has been suggested in WO 01/38362, no specific mention is made about West Nile Virus. The present invention discloses that E1-transformed human cells are able to sustain the growth of West Nile Virus, thereby providing a highly useful tool in the production of large batches of West Nile Virus that are to be used for subsequent purification and inactivation and for use in vaccines.

The present invention relates to methods for producing a West Nile Virus comprising the steps of infecting a cell or a culture of cells with a West Nile Virus; and culturing the cell or the culture of cells obtained in the previous step in a suitable medium under conditions that cause the virus to replicate in the cell or the culture of cells, thereby causing the West Nile Virus to be produced, wherein the cell or the culture of cells is characterized in that it expresses at least an E1A protein of an adenovirus.

In another embodiment of the invention, the invention relates to a method for producing a West Nile Virus comprising the steps of: providing a cell or a culture of cells with nucleic acid coding for the West Nile Virus; and culturing the cell or the culture of cells obtained in the previous step in a suitable medium under conditions that cause expression of the nucleic acid coding for the West Nile Virus, thereby causing the West Nile Virus to be produced, wherein the cell or the culture of cells is characterized in that it expresses at least an E1A protein of an adenovirus. The E1 region of adenovirus comprises several subregions, for example, E1A and E1B. Many studies have been performed in the past that revealed that the different proteins expressed from the E1 region play different roles in transformation of cells and subsequent immortalization to obtain cell lines. The invention, therefore, also relates to a method according to the invention, further characterized in that the cell or the culture of cells expresses at least one protein of the E1B region of an adenovirus. For large-scale production, it is required to have a stable cell line that grows indefinitely. In a preferred embodiment, the invention provides methods according to the invention wherein the cell or the culture of cell comprises a functional E1 region of an adenovirus and wherein the E1 region is stably integrated in the chromosomal genome of the cell.

Different types of cells can be used to apply the methods of the present invention, however, the cell of choice should be a cell that is stable, safe and non-tumorigenic. Therefore, the invention also relates to cells or cultures of cells that are derived from a non-tumorous human cell, and/or derived from a retinoblast, and/or that is derived from an embryonic cell. More preferably, the cell is derived from an embryonic retinoblast. Highly preferred are methods according to the invention in which the cell is a cell as deposited under ECACC no. 96022940 or a derivative thereof. Other cells that may be applied are cells derived from a kidney cell or an amniocyte.

The nucleic acid that is administered to the cells in the methods of the present invention is preferably RNA wherein the RNA is preferably delivered to the cell or to the culture of cells by means of a West Nile Virus.

The West Nile Virus to be produced is preferably lineage II strain West Nile B956, lineage II strain Madagascar 1978, lineage II strain Cyprus 1968, lineage I strain Kunjin 1960, lineage I strain Kunjin 1991, lineage I strain Goose Israel 1998 or lineage I strain New York 1999. In another preferred embodiment, the West Nile Virus strain to be produced is a lineage II strain selected from the group consisting of: Kenya, Uganda, Senegal 1990, Uganda 1937, Uganda 1959, Central African Republic 1972a, Central African Republic 1972b, Central African Republic 1983, Madagascar 1986 and Madagascar 1988. Such West Nile Virus strains may, therefore, also be used to deliver the nucleic acid to the cells or the culture of cells.

Another aspect of the invention relates to methods according to the invention wherein the West Nile Virus is providing the nucleic acid to the cells in a multiplicity of infection ("moi") ranging from 5 to $5 \times 10^{-7}$ plaque-forming units ("PFU") per cell. This range of PFU is sufficient to obtain high titers of replicating West Nile Viruses, as can be seen in the examples herein.

The invention also relates to methods according to the invention further comprising the steps of optionally harvesting the produced West Nile Virus and inactivating the produced West Nile Virus; or to methods according to the invention further comprising the steps of, in either order, inactivating the produced West Nile Virus and harvesting the produced West Nile Virus.

Inactivation of the produced West Nile Viruses is achieved through methods known to a person of ordinary skill in the art. Examples of inactivation are the use of UV-light or the use of beta-propiolactone. A preferred inactivation takes place through the use of formaldehyde (formalin-induced inactivation).

In yet another embodiment, the invention provides methods for obtaining West Nile Viruses that can be used in subunit vaccines; therefore, the invention also relates to a method according to the invention wherein the West Nile Viruses are produced, further comprising the steps of disrupting the produced West Nile Virus, and purifying one or more antigenic components of the West Nile Virus disrupted in the previous step. Such antigenic components are generally the capsid (or envelope) proteins of the West Nile Virus particle, although it cannot be excluded that other (antigenic) proteins, peptides, or entities from the virus can be obtained after using the methods of the present invention. Such products are also encompassed within the claims of the present invention.

The invention also relates to the use of a human cell having a sequence encoding at least the E1A protein of an adenovirus in its genome, which cell does not produce structural adenoviral proteins for the production of a West Nile Virus. Preferably, such cell also comprises at least one E1B sequence coding for an E1B protein and, more preferably, the cell comprises stably integrated into its genome an E1 region from an adenovirus. A highly preferred adenovirus serotype that is used for providing the E1 region is adenovirus serotype 5.

A preferred method according to the invention utilizes a human cell wherein the human cell is derived from an embryonic retinoblast. Highly preferred is the use of a cell as deposited under ECACC no. 96022940, or a derivative thereof.

The invention also relates to the products obtained by the methods of the present invention and to certain applications therewith, such as the use in vaccines. Therefore, it also relates to a West Nile Virus obtainable by a method according to the invention or by a use according to the invention for use in a vaccine, the West Nile Virus being free of any non-human mammalian proteinaceous material, while it also relates to vaccines comprising a West Nile Virus, or a West Nile Virus protein according to the invention, a pharmaceutically acceptable carrier and optionally, an adjuvant. Possible adjuvants that may be applied are mineral oil (generally accepted for veterinary use) or alum-based adjuvants, which may be applied for human use. Pharmaceutically acceptable carriers are widely used and are well known in the art.

To obtain cross-protection, which is a mechanism through which a vaccine based on a relatively harmless virus is used to raise protection against a virus that would normally give rise to a relatively harmful disease, it is preferred to use a vaccine comprising a whole-inactivated lineage II West Nile Virus, a pharmaceutically acceptable carrier and, optionally, an adjuvant. Such vaccines are provided by the present invention.

The invention furthermore relates to a human cell having a sequence encoding at least an E1A gene product of an adenovirus (and, preferably, also a sequence coding for an E1B gene product and, more preferably, an E1 region) in its genome and having a nucleic acid coding for a West Nile Virus. Highly preferred is a human cell according to the invention wherein the human cell is a derivative of a cell as deposited under ECACC no. 96022940, or a derivative thereof.

The invention also provides a method of vaccinating an animal or human subject against West Nile Virus infection, comprising administering a vaccine according to the invention to the animal or human subject.

The present invention relates to a method for producing a West Nile Virus and/or a West Nile viral protein for use as a vaccine, comprising: a) providing a cell having at least a sequence encoding at least one gene product of the E1 region of an adenovirus, with a nucleic acid encoding the West Nile Virus and/or the West Nile viral protein; b) culturing the cell obtained in the previous step in a suitable medium; and c) allowing for expression of the West Nile Virus and/or the West Nile viral protein in the medium and/or the cell. Preferably, the method also comprises the step of purifying the produced West Nile Virus and/or West Nile viral protein from the tissue culture supernatant and/or the cells. Purification steps that can or may be used for obtaining a purified West Nile Virus according to the present invention include (sterile) filtration, chromatography (e.g., using heparin sulphate), diafiltration and/or (an)ion exchange chromatography. Also preferred are methods of the invention comprising the step of inactivating the obtained West Nile Virus. Inactivation is performed by using one or more of the inactivation methods available, such as polysorbate inactivation by, for instance, using TWEEN® 20, TWEEN® 40, TWEEN® 60 and/or TWEEN® 80, and/or by long wavelength ultraviolet radiation, and/or by furocoumarin, and/or by ascorbic acid and/or a salt thereof. Preferably, the West Nile Virus obtained by a method or a use according to the invention is (whole-) inactivated by formalin and/or by beta-propiolactone treatment. The viral RNA may be inactivated by nucleic acid-disrupting agents such as RNase.

The invention also relates to methods for the production of West Nile viral proteins and to the West Nile viral proteins obtained by the methods of the invention. The West Nile viral proteins can be obtained by methods comprising a step of disrupting a West Nile Virus obtained by a method of the present invention, resulting in a subunit of the West Nile Virus. Such a subunit, generally comprising at least one antigenic component of the West Nile Virus, such as the envelope protein(s) and/or fragments thereof, can then be used to produce a vaccine composition. The subunit of the West Nile Virus can also be obtained by methods according to the invention wherein a nucleic acid encoding the subunit is provided to a cell having at least a sequence encoding at least one gene product of the E1 region of an adenovirus, by means other than a West Nile Virus. Therefore, the nucleic acid can be RNA, cDNA and DNA. Preferably, the nucleic acid is RNA and also preferably, the nucleic acid delivery vehicle is a West Nile Virus.

In another preferred embodiment, the cells used for the production of West Nile Virus and/or West Nile viral proteins are cultured in suspension and/or in serum-free conditions. More preferably, the cells are cultured in mammalian component-free medium. Therefore, the invention also relates to methods for producing a West Nile Virus and/or a West Nile viral protein for use as a vaccine, comprising: a) providing a cell with a nucleic acid encoding the West Nile Virus and/or the West Nile viral protein; b) culturing the cell obtained in the previous step in a suitable medium; and c) allowing for expression of the West Nile Virus and/or the West Nile viral protein in the medium and/or the cell, wherein the cell is cultured in suspension (non-adherent). Preferably, a suitable medium for the methods of the present invention is a medium lacking mammalian-derived components or a serum-free medium and, optionally, factors that are recombinantly produced. The growing and culturing of the cells for the methods of the present invention may be performed by using different large-scale set-ups, such as fed-batch, perfusion culture and wave bags.

Providing the nucleic acid may occur during different stages in the cell-culture process and by several different methods such as transfection, electroporation, infection through viral-based delivery (by carriers such as adenoviruses, alphaviruses and poxviruses) or by complexes such as liposomes, or other nucleic-acid delivery vehicles known in the art. Purifying the produced West Nile Viruses and/or West Nile viral proteins according to the methods of the present invention may be performed by several methods known in the art, such as single- or multistep (anion and/or cation) exchange chromatography.

In a preferred embodiment, a method is provided wherein the cell that is provided with the nucleic acid encoding a West Nile Virus or a West Nile viral protein, is derived from a non-tumorous human cell. More preferably, such a cell is derived from a primary human embryonic retinoblast. Even more preferred are methods according to the invention wherein the sequence encoding at least a gene product of the E1 region is present in the chromosomal genome of the cell. Highly preferred is a method wherein the cell provided with the nucleic acid encoding a West Nile Virus is a cell derived from cells such as those that are deposited under ECACC no. 96022940. As a "derivative" thereof can be understood to mean any such cell that contains (in addition to the E1 region of adenovirus serotype 5) another heterologous nucleic acid that may or may not be incorporated in the genome of the cell. Examples of such derivatives are cells that contain, in addition, a temperature-sensitive E2A gene (PER.tsE2A; as described in WO 01/38362) or other adenovirus genes (such as described in WO 02/40665). As "derivatives" can also be understood to mean descendants of cells as deposited under ECACC no. 96022940 that have been sub-cultured for a prolonged period, either under selective pressure and/or mutagenizing agents, or otherwise, since the deposit at the ECACC. It is to be understood that the invention also encompasses other cell lines that have been transformed with at least the E1A region of an adenovirus. Other cell lines that could be used for the present invention comprise, but are not limited to: 293 cells, 293-E4orf6 cells, 911 cells, PER.E1B55K cells, PER.tsE2A cells, HT1080 cells, amniocytes transformed with adenovirus E1, and A549 cells transformed with adenovirus E1.

In another aspect of the invention, the invention provides methods for producing West Nile Viruses and/or West Nile proteins according to the invention, wherein the nucleic acid that is provided to the cell is RNA. Preferably, the nucleic acid is provided by a West Nile Virus, which contains (in its wild-type form) a single (+)RNA strand.

Many strains of West Nile Viruses have been described in the art (Lanciotti et al. 2002). In one embodiment of the present invention, the West Nile Virus that provides the nucleic acid to the cell and/or that is the West Nile to be produced, is strain West Nile B956 (lineage II). Lineage II West Nile strains are normally not related to human illnesses, while lineage I strains are or can be (Lanciotti et al. 2002). The strains that may be produced with methods according to the invention are given in Table I. More West Nile Virus strains not given in Table I may also be produced with the methods of the present invention. Preferably, New York 1999 (also referred to as NY99 or USA99b, see below; several isolates were reported from the New York area, ranging from human, equine and avian sources), Israel 1998 (Goose Israel 1998, sometimes referred to as Isr98 or IS-98-ST1, see WO 02/081511), NY2000 3282, NY2000 3356, NY 1999 equine, Conn 1999, MD 2000, NJ 2000, Kunjin 1960 or 1991 (Aus6O or Aus9l respectively, also referred to as strains MRM 16 or K 6453 respectively, see below), Madagascar 1978, Cyprus 1968 and Israel 1999 H are used for the methods of the present invention. In one preferred embodiment, West Nile Virus strain NY 1999 hum (a strain isolated from a human brain in 1999 in the New York area) or 385-99 (a strain isolated from the organs of a Snowy Owl, *Nyctea scandiaca,* of The Bronx Zoo in the New York outbreak) is produced using methods of the present invention. It is to be understood that it is also feasible to grow chimeric flaviviruses known in the art (WO 98/37911; WO 01/39802; WO 01/60847; EP 0102228 A; EP 0872553 A; U.S. Pat. No. 6,184,024) by methods of the present invention, thereby circumventing possible problems of low titers, high costs and/or safety issues.

In a specific embodiment, the present invention provides methods according to the invention wherein a West Nile Virus is providing the nucleic acid to the cells in a multiplicity of infection ("moi") ranging from 5 to $5\times10^{-7}$ plaque-forming units per cell. As shown in the examples, the inventors of the present invention were able to show that it is feasible to obtain titers of $10^9$ pfu/ml after three days following an moi that was as low as 0.005 pfu/cell, using methods of the present invention, while titers obtained with a higher moi, were most likely even higher.

In one embodiment, the invention relates to the use of a human cell having a sequence encoding at least one E1 protein of an adenovirus in its genome, which cell does not produce structural adenoviral proteins for the production of a West Nile Virus or at least one West Nile viral protein. Preferably, the human cell is derived from a primary retinoblast and, even more preferred, are uses according to the invention, wherein the human cell is a cell as deposited under ECACC no. 96022940, or a derivative thereof.

In another embodiment, the present invention relates to a West Nile Virus or a West Nile viral protein obtainable by a method according to the invention, or by a use according to the invention, for use in a vaccine, the West Nile Virus or the West Nile viral protein being free of any non-human mammalian proteinaceous material. A vaccine may be produced with a West Nile Virus and/or West Nile Virus protein according to the invention. Such a vaccine is preferably a composition comprising a West Nile Virus and/or a West Nile viral protein obtained and a suitable (pharmaceutically acceptable) carrier such as regularly used in the art of preparing vaccine compositions for use in humans and in veterinary applications. Optionally, the vaccine also comprises an adjuvant. Preferably, the human vaccine comprises an adjuvant reagent that is acceptable for use in humans, such as "Alum" or aluminum hydroxide, which is an adjuvant known to persons skilled in the art. Another adjuvant that may be applied is aluminum phosphate. For veterinary use, it is also preferred to use an adjuvant, for example Mineral Oil. Mineral Oil is an adjuvant that is widely applied in the veterinary vaccine industry, for instance, in the West Nile Virus vaccine produced on mouse brains that has been approved in Israel for vaccination of geese. The vaccine of the present invention is applied for prophylactic, therapeutic and/or diagnostic use. The vaccine according to the invention is also applied for cross-vaccination for viruses that are highly similar to West Nile Virus within the Flaviviridae family. For safety reasons, it is preferable to vaccinate animals and human subjects against West Nile Virus by using a vaccine comprising a whole-inactivated Lineage II strain (associated with mild disease), thereby protecting such individuals against a lineage I strain infection (associated with severe disease) via a mechanism known as cross-protection. It is thus a highly preferred embodiment of the present invention to produce a vaccine based on a Lineage II strain that gives cross-protection against a Lineage I West Nile Virus in animals as well as in humans. The B956 strain (Lineage II) is just one example of such a strain, but those of skill in the art would be able to identify other strains related to mild disease-causing strains and belonging to the Lineage II strains (for instance, those given in Table I) that provide cross-protection against severe disease-causing strains upon vaccination with a vaccine comprising the mild disease-causing strain. Other preferred lineage II strains are Madagascar 1978 and Cyprus 1968.

In another embodiment, the invention relates to a human cell having a sequence encoding at least one E1 gene product of an adenovirus in its genome and having a nucleic acid encoding a West Nile Virus. Preferably, the human cell having a sequence encoding at least one E1 gene product of an adenovirus in its genome and having a nucleic acid encoding a West Nile Virus is the cell line as deposited under ECACC no. 96022940, or a derivative thereof.

EXAMPLES

Example 1

Infection of Cells with Strain West Nile B956

Cells (as deposited under no. 96022940 at the European Collection of Animal Cell Cultures at the Centre for Applied Microbiology and Research) and useful in technologies as marketed as a platform by Crucell Holland B.V. under the trade name PER.C6®, were banked and cultured as described (WO 01/38362). A series of cells were cultured in T80 culture flasks with $10^7$ cells per flask and several dilutions of West Nile Virus were incubated with these cells. The strain that was used was West Nile B956 (lineage II) (Yamshchikov et al. 2001). The virus was plaque purified on Vero cells using techniques known to persons skilled in the art of growing viruses and the virus was further produced on BHK cells. A plaque assay was performed on Vero cells to determine the viral titer of the starting material in the BHK supernatant. This plaque assay was performed according to the general methods applied in the art. This titer appeared to be $5\times10^8$ plaque-forming units per milliliter (pfu/ml). A mock-transfection was performed using dilution buffer (DMEM/5% FBS non-Heat Inactivated [nHI]). Post-infection, samples were taken each day for "real time" reverse transcriptase TAQMAN® PCR analysis (Applied Biosystems, CA) (Lanciotti et al. 2000) to determine the titer of the virus produced, for Reverse Transcriptase (RT) PCR, and for Immune Fluorescence. RT-PCR and TAQMAN® PCR was performed using West Nile Virus specific primers (see below).

The input virus was diluted in DMEM/5% FBS nHI and incubated for 1 hour with the PER.C6® cells in eight serial dilutions ($10^{-1}$ to $10^{-8}$, with an moi of 5 to $5 \times 10^{-7}$ pfu/cell). After incubation of the virus with the cells, the culture medium was discarded and replaced with fresh DMEM/5% FBS nHI (not-Heat Inactivated). Cells were cultured at 37° C./10% $CO_2$ at all times. Cytopathological effect (CPE) was scored visually after 24 hours, 48 hour and 72 hours post-infection. Results are shown in Table II. No CPE was detected at 24 hours post-infection. However, clear CPE was visible at the highest occurrences moi after 48 hours, while in most cases significant CPE was detected at 72 hours post-infection. These results show clearly that E1-transformed human cells, such as PER.C6® cells, are able to sustain the production of West Nile Viruses.

Example 2

RT-PCR on Adenovirus E1-transformed Human Embryonic Retina Cells Infected with West Nile Virus Reverse Transcriptase Polymerase Chain Reaction (RT-PCR) was performed on the mock-transfected cells as deposited under ECACC no. 96022940 and on the 24-hour and 48-hour post-infection samples of such cells infected with an moi of $5 \times 10^{-1}$ and $5 \times 10^{-4}$ pfu/cell. RNA samples were diluted 1:10, 1:100 and 1:1000. RT-PCR was performed by using the QIAGEN® One-Step RT-PCR Kit (QIAGEN®) and general methods known to persons skilled in the art of molecular biology. The primers used were forward primer WNV 1: 5'-CCA CCG GA(A/T) GTT GAG TAG ACG-3' (SEQ ID NO:1) and reverse primer WNV 2: 5'-TTT G(T/G)T CAC CCA GTC CTC CT-3' (SEQ ID NO:2). The negative control solely contained water, while the positive control contained input virus from the BHK supernatant. The PCR program that was used was as follows: 30 minutes at 50° C., 15 minutes at 95° C., followed by 35 cycles of 30 seconds at 94° C., 30 seconds at 50° C. and 1 minute at 72° C. and a final step minutes at 72° C. Obtained amplified nucleic acid was loaded on a gel and visualized. Results show that West Nile viral RNA is present in all samples of cells that were infected with West Nile Virus, while no positive signal could be detected in the mock infections (FIG. 1). The amount increases from 24 hours to 48 hours post-infection in the lower moi sample.

Example 3

Immune Fluorescence Staining of Cells as Deposited Under ECACC No. 96022940 Infected with West Nile Virus Samples were obtained 48 hours post-infection from the cells as deposited under ECACC no. 96022940 that were mock-infected and that were infected with an moi of $5 \times 10^{-3}$ (see Table II) with West Nile Virus B956. These samples were used for immune fluorescence using, as a negative control, normal human serum and, as a positive antiserum, a Monkey-derived antiserum directed against the envelope of another flavivirus, namely Yellow Fever virus. Yellow Fever virus is highly similar to West Nile Virus and the antiserum generally also recognizes the envelope of the West Nile Virus. The serum was obtained after injection of Yellow Virus in a monkey and recovery of the serum. Fixing with acetone and staining procedures were performed according to general methods known in the art and by using a standard fluorescence microscope. Although the human serum gave a relatively high background, a positive signal could be determined on the cells stained with the monkey antiserum as can be seen in FIG. 2. These results indicate that West Nile Virus is able to infect human adenovirus E1-transformed cells, such as PER.C6® cells.

Example 4

Real-time TAQMAN® PCR for the Detection and Quantification of West Nile Virus RNA in Infected PER.C6® Cells To determine the titers of the West Nile Virus that were produced by the cells as deposited under ECACC no. 96022940, a real-time reverse transcriptase TAQMAN® PCR was performed on all samples, except for the 72-hour post-infection samples of the three highest occurrences of moi as shown in Table II.

RNA was extracted using the spin protocol of the QIAamp Viral RNA Mini Kit (QIAGEN®) following the description provided by the manufacturer. 200 µl cell culture supernatant was mixed with 60 µl elution volume. Amplification and real-time detection was performed using the MASTER-MIX™ without UNG with the RNase Inhibitor Mix (Applied Biosystems) and the QUANTITECT® Probe RT-PCR Kit (QIAGEN®) using the forward primer WNV 1 and reverse primer WNV 2, and with the VIC-labeled probe: 5'-VIC-TGC TGC CTG CG(A/G) CTC AAC CC-TAMRA-3' (SEQ ID NO:3). All protocols were performed using the instructions provided by the manufacturers and generally following the methods as described by Hadfield et al. (2001) and Lanciotti et al. (2000). Concentrations used were: Forward primer 300 nM, Reverse primer 900 nM and VIC-labeled probe 100 nM.

Results are shown in Table III. Clearly, PER.C6® cells are able to sustain growth of at least a titer of $1 \times 10^9$ pfu/ml using an input moi of $5 \times 10^{-3}$ pfu/cell, 72 hours post-infection, while probably even higher titers were obtained in lower dilutions. This indicates that PER.C6® is a very useful tool for the production of West Nile Viruses. Since it has been shown that PER.C6® cells can grow to very high densities in serum-free medium in suspension and in large incubators (>1000 liter), it is now possible to obtain very large batches of West Nile Virus that can be used for inactivation and subsequent use in vaccines against West Nile viral infections and, most likely, also against other flavivirus infections due to cross-vaccination. The obtained West Nile Viruses can also be used to disrupt and, thus, to make split vaccines or to purify separate subunits from the disrupted virus, such as envelope proteins for use in the so-called subunit vaccines. Methods for disrupting enveloped viruses are known to the skilled person.

Example 5

Figure 4:
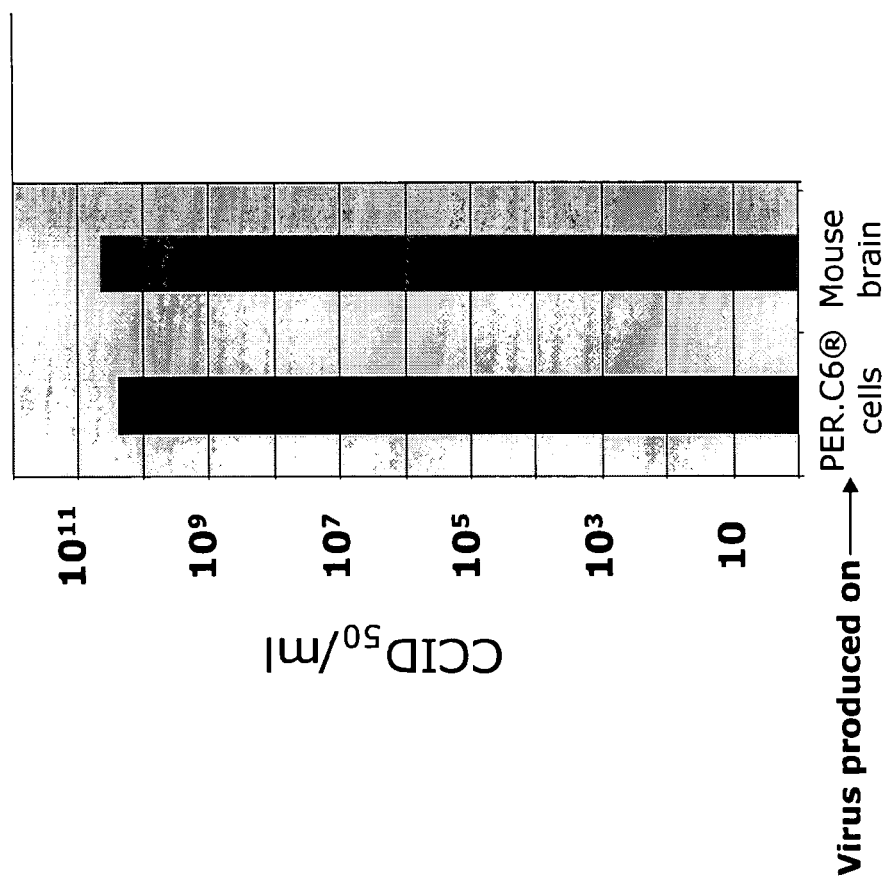
FIG. 4 is a diagram showing the titer of the virus preparation produced on cells as deposited under ECACC no. 96022940 and in Mouse Brain. The titration was determined using VERO cells and given in CCID50/ml.

Production of West Nile Virus Strain Goose Israel 1998 on Human Adenovirus E1-transformed Cells for an Animal-challenge Model in Geese Cells as deposited under ECACC no. 96022940 were banked and cultured as described (WO 01/38362). West Nile Virus strain Goose Israel 1998 (Malkinson et al. 1998 and 2001; Lanciotti et al. 1999) was produced by inoculating sub-confluent (80%) monolayers of such cells, grown in T175 flasks in DMEM plus 10% Fetal Bovine Serum, with the virus at an moi of 0.001 virus particles ("vp") per cell. The virus-containing culture supernatant was harvested at day 6 post-infection and cleared by centrifugation. The resulting virus preparation was titrated on Vero cells, using methods known to persons skilled in the art, and seeded in 96-well plates following standard procedures (Bin et al. 2001; Malkinson et al. 2001). The titer was determined to be $10^{10.66}$ or $4.57 \times 10^{10}$ $CCID_{50}$/ml (Cell Culture Infectious Dose 50 per ml) for the virus produced on cells as deposited under ECACC no. 96022940 and $10^{10.83}$ or $6.76 \times 10^{10}$ $CCID_{50}$/ml for the virus produced on mouse brain. The results of the titration on Vero cells are given in FIG. 4.

Figure 5:
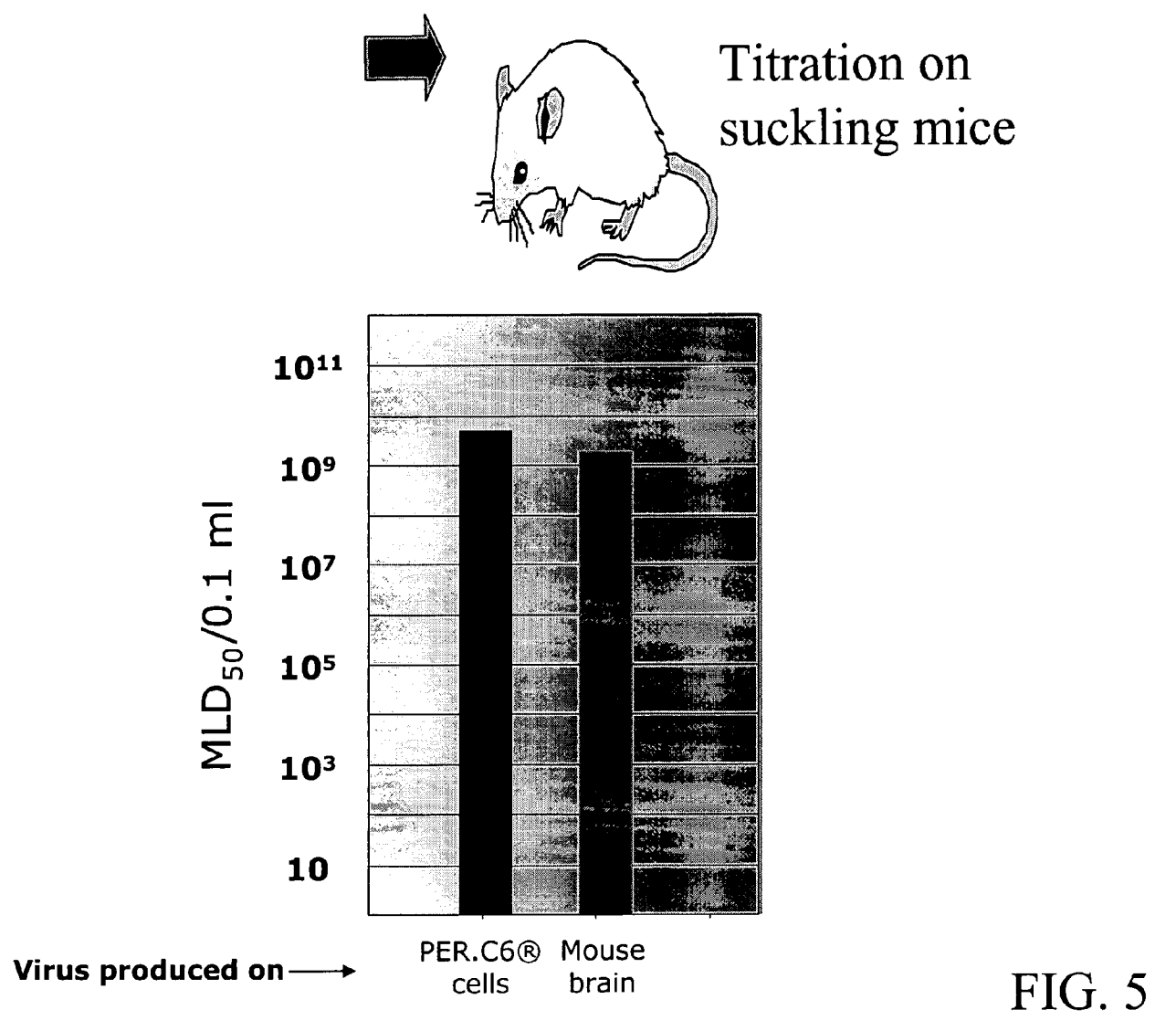

The virus preparation was also titrated in suckling mice by intra-cranial (i.c., NB: i.c. may also indicate intra-cerebrally; all i.c. injections were meant to be directly in the brain) injection of 0.03 ml of ten-fold serial dilutions of the culture supernatant. Mice were observed for mortality over a 9-day period. The mortality titer for the PER.C6®-produced viruses was found to be $10^{9.76}$ $MLD_{50}$/0.1 ml (mouse lethal dose 50 per 0.1 ml), while the titer of the virus preparation from mouse brain was found to be $10^{9.63}$ $MLD_{50}$/0.1 ml, as shown in FIG. 5.

The virus preparation was inactivated by adding 1 ml formaldehyde (stock solution of 4%) to 100 ml virus-containing PER.C6® supernatant and by stirring this solution at 4° C. for four weeks. Inactivation was checked by titration of the inactivated material in suckling mice as follows: 0.03 ml of inactivated antigen was injected i.c. in suckling mice, which were subsequently observed for 14 days for mortality. No mortality was observed in any of the animals. Thus, it is shown here that E1-transformed cells can sustain the growth of the Goose Israel 1998 West Nile Virus strain to very high titers and that the produced West Nile Viruses can be inactivated sufficiently by the treatment of formaldehyde.

Example 6

Animal Vaccination/Challenge Study Using a PER.C6®-produced West Nile Vaccine in Comparison with a Mouse Brain-produced Vaccine Two-week-old geese were vaccinated subcutaneous on day 0 and boosted with the same volume on day 14 according to the scheme as depicted in Table IV. General methods were as described by Malkinson et al. (2001), while the Mouse brain vaccine (serving as a positive control) was produced as also described by Malkinson et al. (2001). Mineral oil, which is a common additive in veterinary vaccines and used as an adjuvant, was blended with the preparation and used to form a suitable vaccine/adjuvant mixture. Some groups receiving the inactivated virus produced on PER.C6® received no mineral oil, while the positive control group did, as shown in Table IV. Although Mineral Oil is a well-recognized adjuvant in the art of veterinary vaccines, it is unlikely to be used in humans. Therefore, it is also an aspect of the invention to prepare vaccines comprising adjuvant reagents that are acceptable for use in humans. An example of such an adjuvant is "Alum," or aluminum hydroxide, also known to persons skilled in the art. It is to be understood that all adjuvant reagents that are acceptable for use in humans can or may be used with the inactivated West Nile Viruses according to the present invention.

All animals were challenged with West Nile Virus strain Goose Israel 1998 at day 21 after the boost injection (day 35 from start of vaccination). Animals were observed daily for signs of disease and mortality for a period of three weeks after challenge. Blood samples were taken from all animals before each vaccination and boost and before challenge and from animals surviving the challenge after three weeks.

Figure 6:
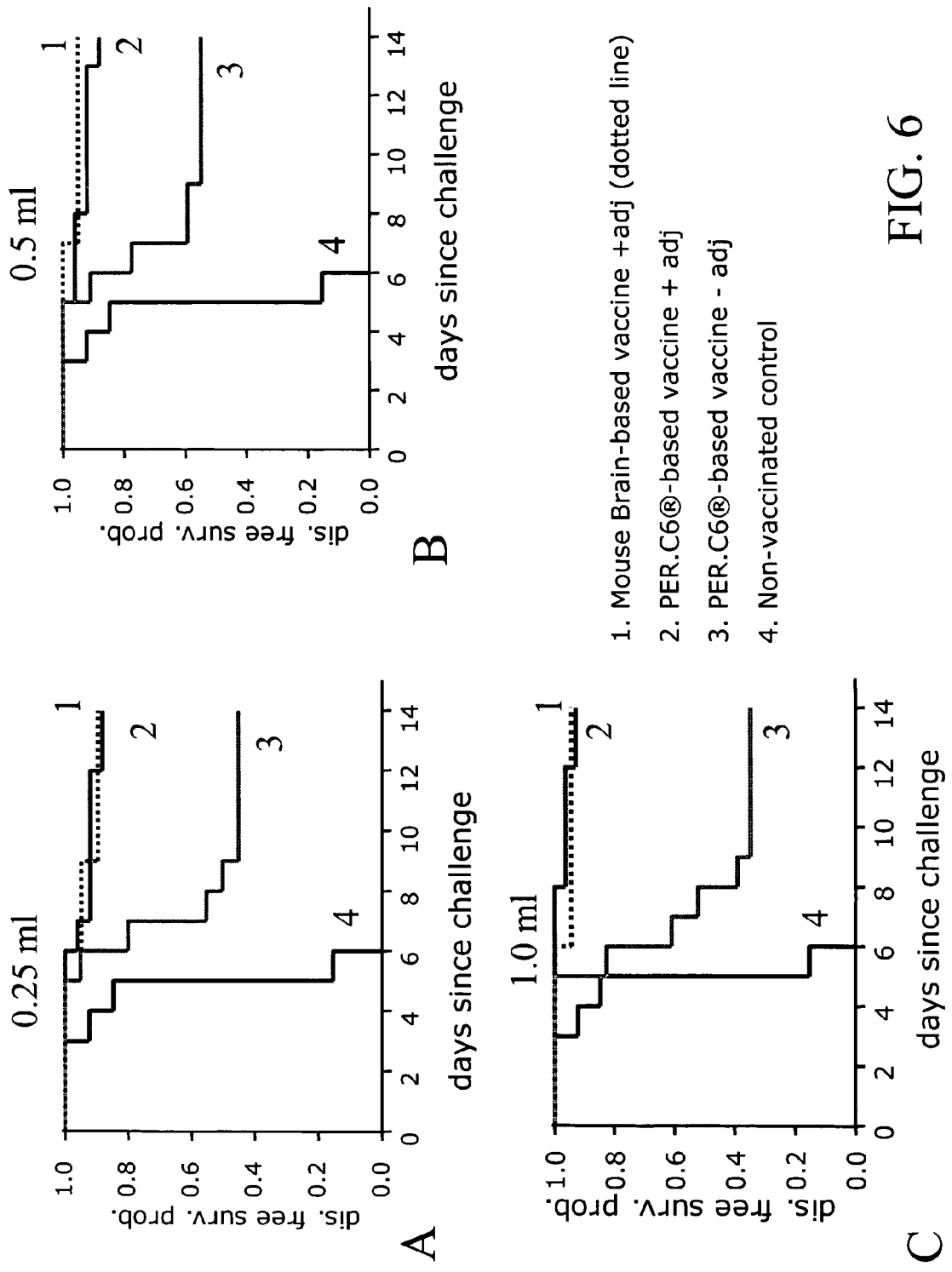
FIG. 6 are diagrams showing the time to disease or death of the geese challenged with the West Nile Virus strain Goose Israel 1998, vaccinated with a volume of 0.25 ml (A), 0.5 ml (B) or 1.0 ml (C) as compared to the control geese that did not receive vaccination (negative control); given here as line "4." The vaccine comprising the inactivated West Nile Virus produced on mouse brain was taken as a positive control and given as a dotted line "1." The PER.C6®-based vaccine including the adjuvant is represented by line "2," and the PER.C6®-based vaccine without adjuvant is represented by line "3."
Figure 7:
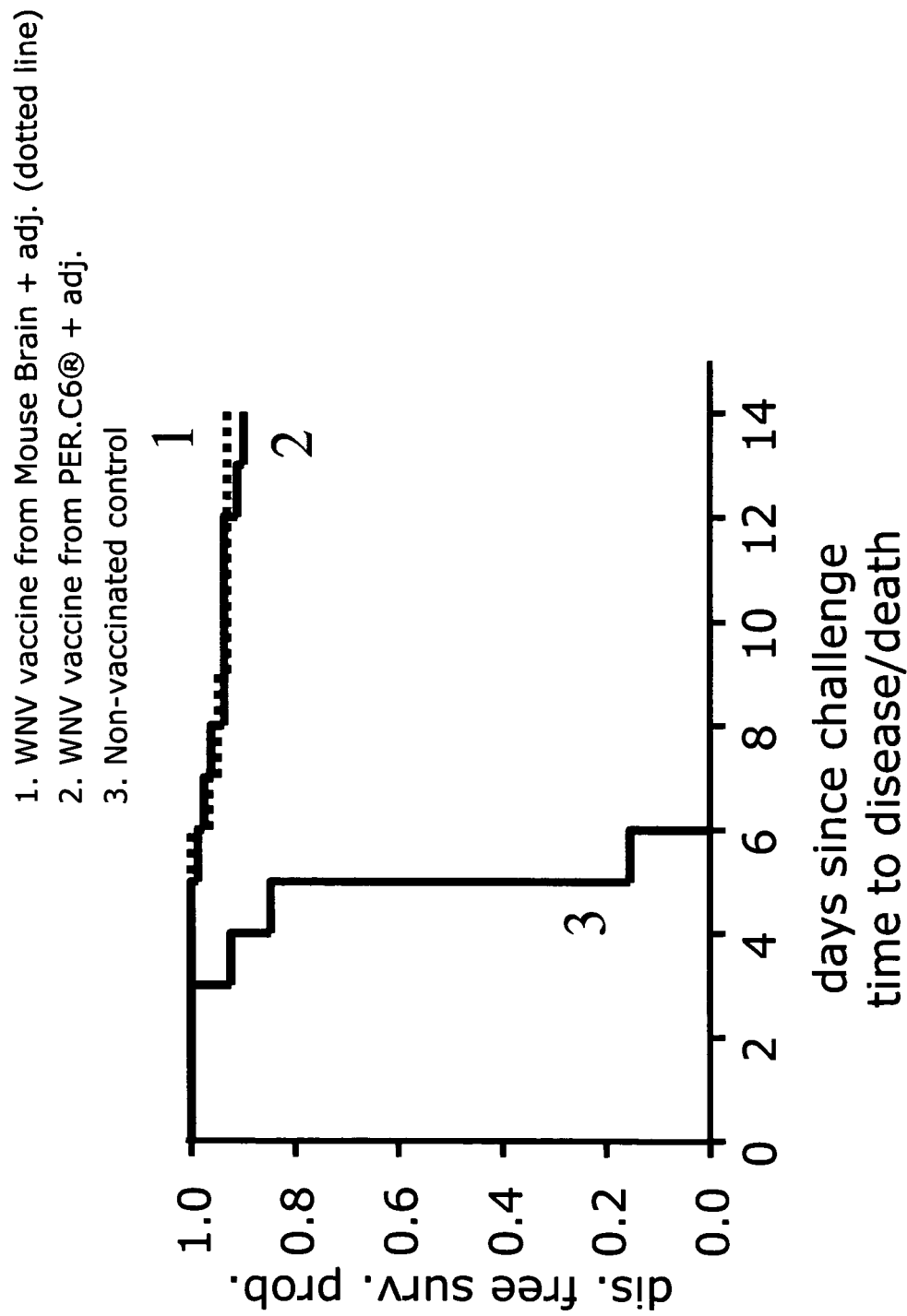
FIG. 7 is a diagram showing the time to disease or death of all geese combined from the three volumes of FIG. 6. Line "1" (dotted) represents the vaccine with the inactivated West Nile Virus produced on mouse brain. Line "2" represents the PER.C6®-based vaccine including the adjuvant and "3" is the negative control. The group receiving the PER.C6®-based vaccine without adjuvant is not given here.
Figure 8:
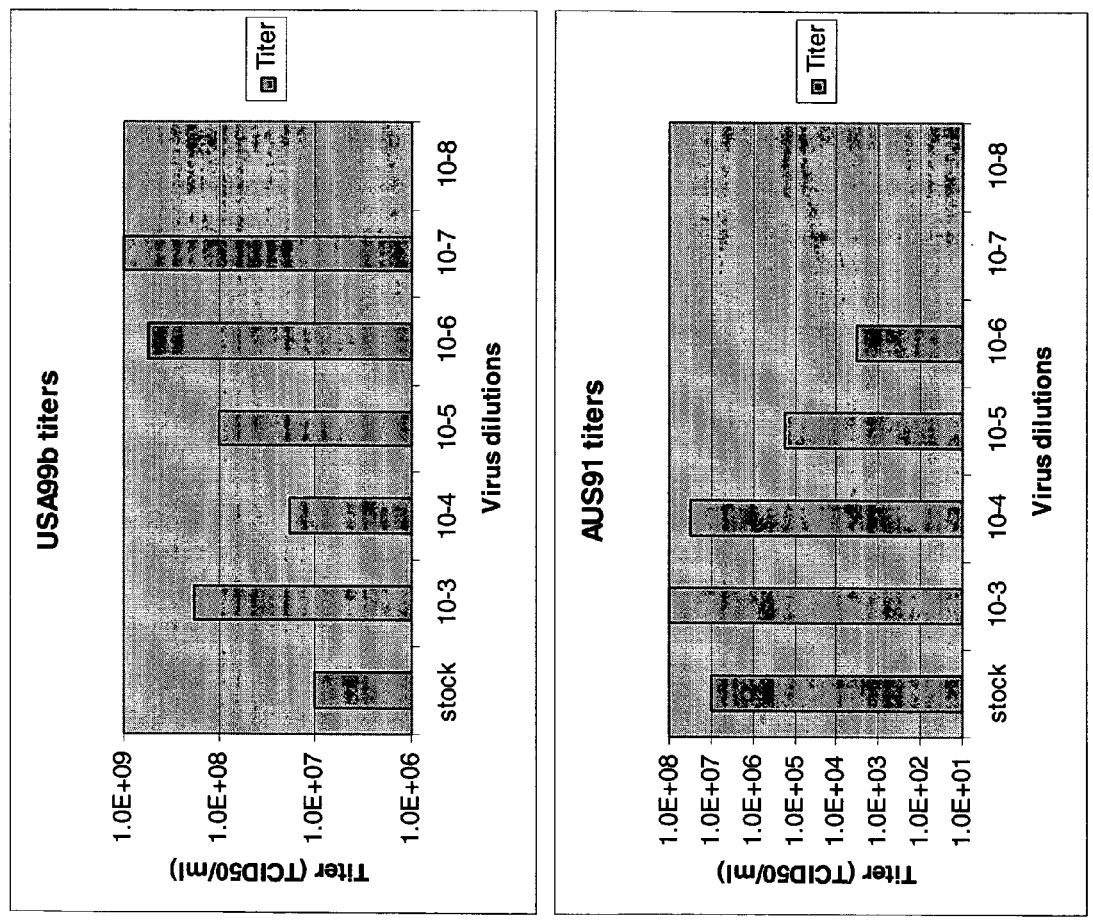
FIG. 8 shows the TCID50 titers obtained with several West Nile Virus strains grown on cells as deposited under ECACC no. 96022940, using different dilutions of virus: (A) New York 1999 (USA99b); (B) Kunjin 1991 (Aus91); (C) Madagascar 1978 (Mad78); (D) Kunjin 1960 (Aus60); (E) Cyprus 1968 (Cyp68); (F) Goose Israel 1998 (Isr98).
Figure 8:
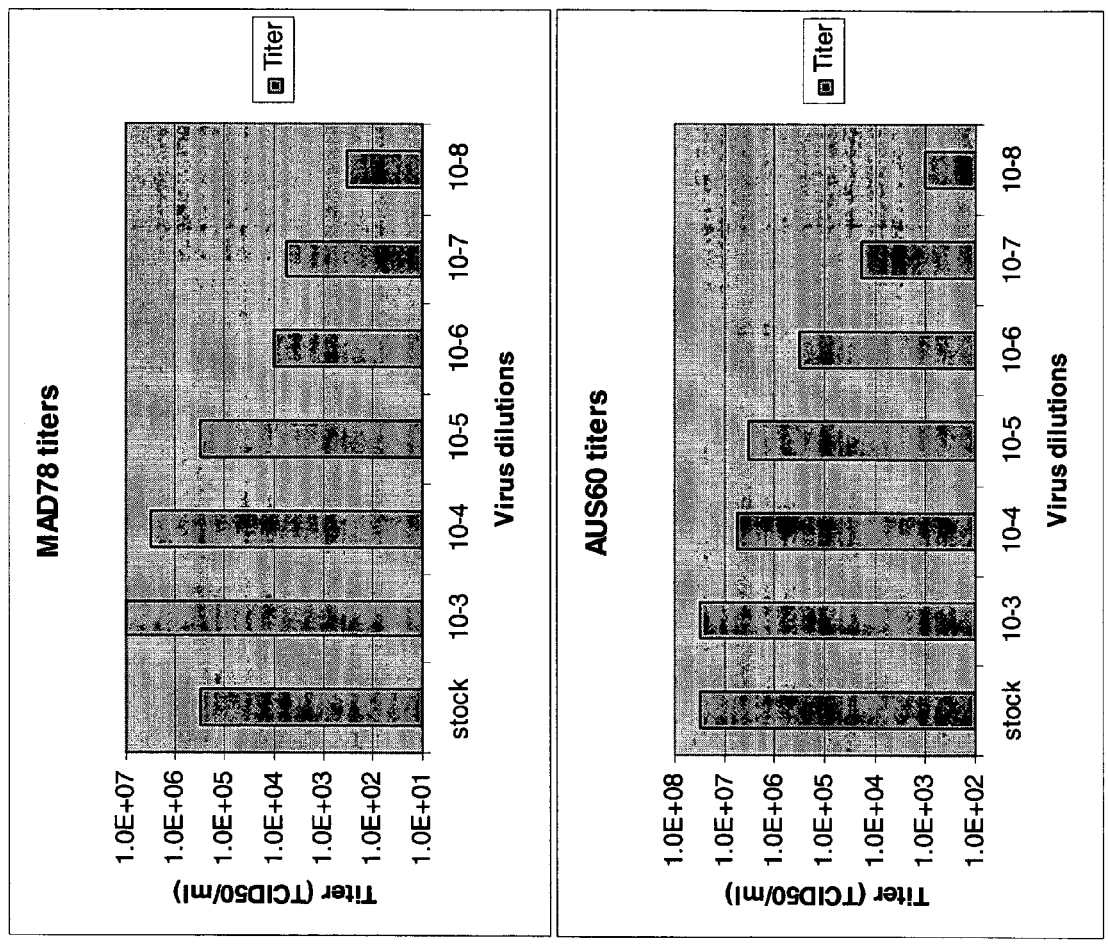
Figure 8:
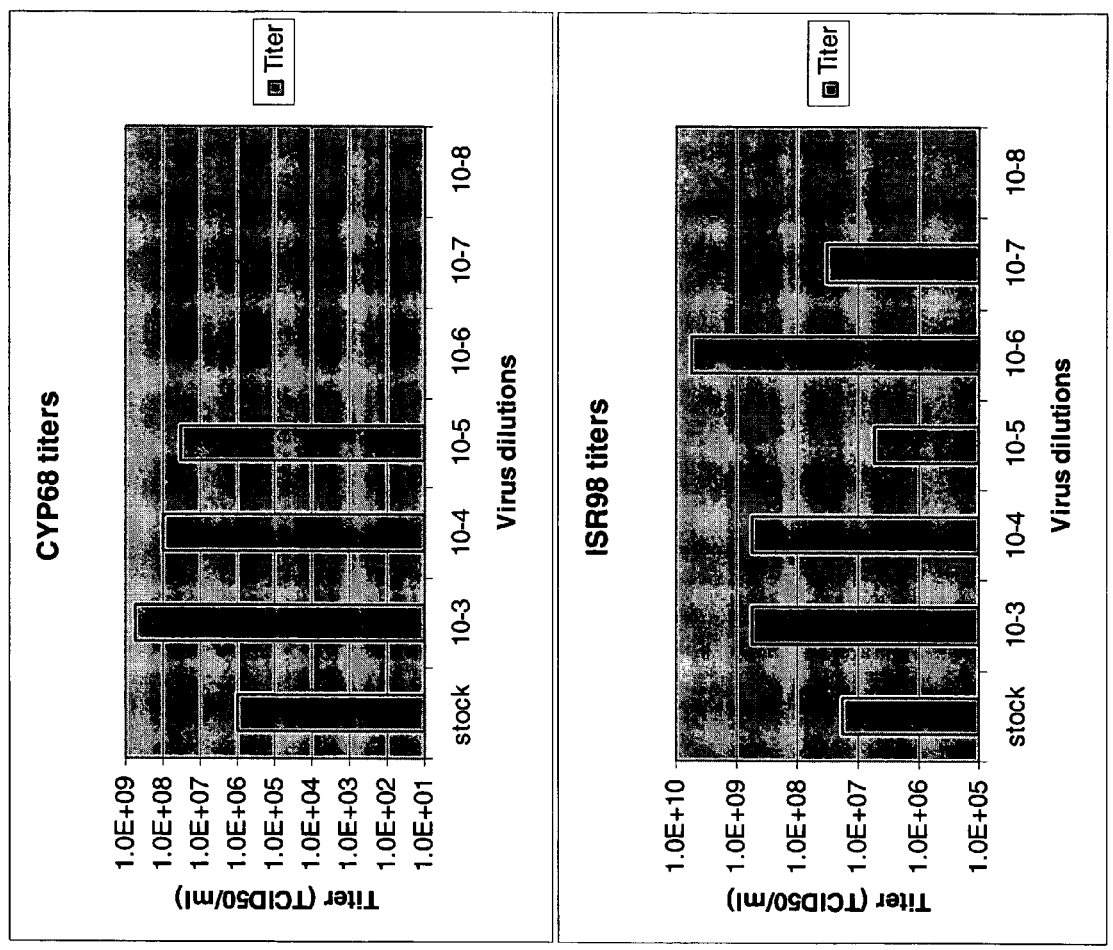

The results of these experiments are shown in Tables V and VI and clearly indicate that the PER.C6®-produced West Nile Viruses (in an inactivated form and in the combination with an adjuvant) are as potent as the vaccine produced on Mouse Brain. The survival rate in the animal groups receiving PER.C6®-based vaccine plus mineral oil ranges from 88% to 92.3% (with all three groups averaged to 89.7%, which equal 70 animals out of 78 being disease free), while the Mouse Brain-based vaccine plus mineral oil ranges from 89.5% to 95% (with all three groups averaged to 93%, which equals 53 animals out of 57 being disease free). Whether the difference is significant between the rates found with the PER.C6® versus the Mouse Brain-based vaccine cannot be determined since the number of animals in both groups is too low. The percentage of survival in the negative control group was 0%, which is a significant difference compared to the groups that received a vaccine; all animals in the negative control group died within six days upon challenge. The results are also depicted graphically in FIG. 6 for the three separate volumes used (FIG. 6A: 0.25 ml; FIG. 6B: 0.5 ml; and FIG. 6C: 1.0 ml). The group receiving the Mouse Brain-based vaccine is indicated with a dotted line 1, the group receiving the PER.C6®-based vaccine+adjuvant is indicated with line 2, the group receiving the PER.C6®-based vaccine minus adjuvant is indicated with line 3, and the negative control group is indicated with line 4. FIG. 7 shows the results summarized in Table VI for the three volume groups taken together and also clearly indicates that the PER.C6®-based vaccine (line 2) is as potent as the Mouse Brain-based vaccine (dotted line 1) as compared to the negative control (line 3) in this goose model.

Example 7

Cross-protection Using Different Lineage I and II West Nile Virus Strains in an Animal Study The West Nile Virus strains depicted in Table VII are used in a cross-protection study to prevent disease. This is to investigate the possibility of obtaining cross-protection against a Lineage I strain (associated with severe disease) by using a vaccine based on a Lineage II strain (associated with mild disease), when the vaccine is made of inactivated West Nile Viruses produced in E1-transformed cells such as PER.C6®. Some strains exhibit very low neuroinvasion ability when administered intra-peritoneal (i.p.), while others do better. For instance, it is known from the art that the NY 99 (Lineage I) strain has a $LD_{50}$ (Lethal Dose 50) of only 0.5 plaque-forming units (pfu) when administered i.p., while other strains such as Kunjin 1960 (Lineage I) and Cyprus 1968 (Lineage II) have a $LD_{50}$ dose of more than 10,000 pfu when administered i.p. If the viruses are administered intra-cranially, no large difference in neurovirulence is found. These aspects of these strains are known in the art.

Because of safety reasons, it is preferable to use a Lineage II strain for the production of a vaccine that will give protection against disease caused by Lineage I strains. For this, the strains depicted in Table VII were all grown on PER.C6® and were subsequently inactivated as described above. The inactivated viruses are mixed with the appropriate adjuvant (most likely mineral oil for geese) and used in a vaccination/boost/challenge study as previously outlined. Different groups of animals are used for the different vaccines, while the challenge is performed with the Goose Israel 1998 and the New York 1999 (NY 99) strains. If a Lineage II strain-based vaccine gives sufficient protection against a Lineage I virus challenge and if the passage history of the preferred strain is acceptable (for safety reasons), such strain is preferably the basis for a vaccine that is to be used in humans.

Infection of cells as deposited under ECACC no. 96022940 with the different West Nile Virus strains was generally performed as follows. Cells were trypsinized, counted, and seeded in 25 cm$^2$ flasks using 5×10$^6$ cells per 5 ml DMEM, 5% FBS medium per flask. Cells were incubated for 24 hours at 37° C. under 10% $CO_2$. Before infection, the medium was replaced with fresh DMEM +5% FBS. The general assumption is that the cell number is doubled since seeding, after which the multiplicity of infection (MLD50 or TCID50/cell) could be determined. The viruses were then added and incubated with the cells at 37° C. 10% $CO_2$ for several days. When full cpe had occurred, cells and medium were harvested and supernatant was clarified by centrifugation, 10 minutes at 2000 rpm. Subsequently, virus titers were determined for different virus dilutions. Results regarding cpe are depicted in Tables VIII to XIII, while the TCID50 titers obtained using the different virus dilutions are given in FIGS. 8A to F. The highest titers in TCID50/ml for each strain were (with the specific input moi between brackets):

USA99b: $1\times10^9 (5\times10^{-7})$
Isr98: $5.6\times10^9 (8.9\times10^{-6})$
Mad78: $1\times10^7 (1.6\times10^{-4})$
Cyp68: $5.6\times10^8 (5\times10^{-4})$
Aus60: $3.2\times10^7 (1.6\times10^{-2})$
Aus91: $1\times10^8 (5\times10^{-3})$.

These results show that all tested West Nile Virus strains grow on PER.C6® to significant titers using a relatively low moi, albeit with different efficiencies. The best harvest days seem to be day 5 or day 6 but this may depend on the culture set-up, the density of the cells, media, scale, and other culture conditions.

Example 8

Protection Study Using Whole-Inactivated Vaccines with West Nile Virus Produced on PER.C6® in Combination with Different Adjuvant Compounds A double-blind vehicle-controlled study to assess the effect of aluminum hydroxide and aluminum phosphate adjuvants on the efficacy of a PER.C6®-based West Nile vaccine in geese was performed. In a previous proof of concept experiment, full protection of geese by vaccination with a PER.C6®-based experimental WN vaccine was found using mineral oil as adjuvant (see Example 6). However, mineral oil cannot be used in vaccines for human applications. This implicates the requirement of testing alternative adjuvants that were previously approved for human use.

Aluminum-based adjuvants have been used for decades to increase the immune response of vaccines for human and animal use. Two types of aluminum-based adjuvants, REHYDRAGEL® aluminum hydroxide and REHYDRAPHOS® aluminum phosphate were tested for the immune potentiating effect in PER.C6®-based West Nile Virus vaccines. The endpoint was a percentage of disease-free survival in the test groups with adjuvant that was twice the percentage of that obtained in the group without adjuvant. Apart from investigating the effect of aluminum-based adjuvant, the study aimed at confirming the results of the previous study, using larger group sizes of geese and a double-blind set-up.

The bulk of the material of the West Nile Virus produced on mouse brain in this study was produced as described (Malkinson et al. 2001) and titrated on VERO cells. The titer of this control vaccine was $10^{10.25}$ TCID50/ml and referred to as Mouse Brain-MV.

The PER.C6®-based West Nile Virus bulk was produced by inoculating sub-confluent (80%) monolayers of PER.C6® cells, grown in T175 flasks in DMEM with FBS, with strain Goose Israel 1998 (Mouse brain-derived) at an moi of $10^{-3}$. The virus-containing culture supernatant was harvested at day 6 post-infection and clarified by centrifugation at 1000 RPM for 20 minutes. The resulting virus preparation was titrated on VERO cells seeded in 96-well plates. The titer was $10^{10.66}$ TCID50/ml. The virus preparation was subsequently titrated in suckling mice by intra-cranial injection of 30 µl, ten-fold serial dilutions of the culture supernatant. Mice were observed for mortality over a nine-day period. The titer was $10^{9.76}$ MLD50/ml and referred to as PER.C6®-WN.

A batch of supernatant from PER.C6® cells was produced under similar conditions as for PER.C6® cells infected with West Nile Viruses. However, for this, cells were not infected ("Sham"-infected). Supernatant was harvested and clarified by centrifugation. This preparation was used as a negative control and referred to as PER.C6®-SH.

The West Nile Virus bulk preparations from PER.C6® and the supernatant of Sham-infected PER.C6® cells were inactivated by adding 1 ml formaldehyde (stock solution of 4%) to 100 ml virus-containing PER.C6® supernatant and by stirring at 4° C. for four weeks. Inactivation of the Mouse Brain-WN was performed using methods known in the art. Inactivation was controlled by titration of the inactivated material in suckling mice. To this end, 30 µl of ten-fold serial dilutions ($10^{4.0}$-$10^{10.0}$) were injected intra-cranial in suckling mice. The animals were subsequently observed for mortality over nine days. The resulting titers were sufficiently low; no live harmful virus was detectable using this animal test assay.

PER.C6®-WN was formulated with REHYDRAGEL® LV containing 2% $Al_2O_3$ (Reheis) as follows: 98.75 ml of DMEM, 5% FBS was added to 35 ml of clarified inactivated virus bulk (pH 7.2-7.4) and mixed in a clean, sterile 250 ml bottle. Subsequently, 6.25 ml of REHYDRAGEL® LV was added. The solution was manually swirled and then set on an orbital shaker set at 90 rpm for 1 hour 25 minutes at 20° C. The formulated vaccine, referred to as PER.C6®-WN-AlOH, was then aliquoted aseptically at 23 ml/vial (six vials) and stored at 4° C.

PER.C6®-WN was formulated with REHYDRAPHOS® containing 2% solid aluminum phosphate (Reheis) as follows: 98.75 ml of DMEM, 5% FBS was added to 35 ml of clarified inactivated virus bulk (pH 7.2-7.4) and mixed in a clean, sterile 250 ml bottle. Subsequently, 6.25 ml of REHYDRAPHOS® was added. The solution was manually swirled and then set on an orbital shaker set at 90 rpm for 1 hour 25 minutes at 20° C. The formulated vaccine, referred to as PER.C6®-WN-AlPh, was then aliquoted aseptically at 23 ml/vial (6 vials) and stored at 4° C.

PER.C6®-WN was formulated as follows to obtain a vaccine without adjuvant: 105 ml medium was added to 35 ml of clarified inactivated virus bulk (pH 7.2-7.4) in a clean, sterile 250 ml bottle. The solution was manually swirled and then set on an orbital shaker set at 90 rpm for 1 hour 25 minutes at 20° C. The vaccine was then aliquoted aseptically at 23 ml/vial (six vials) and stored at 4° C.

PER.C6®-SH was formulated with REHYDRAGEL® as follows: 33.85 ml medium was added to 12 ml of clarified inactivated virus bulk (pH 7.2-7.4) in a clean, sterile 100 ml bottle. Subsequently, 2.15 ml of REHYDRAGEL® LV was added. The solution was manually swirled and then set on an orbital shaker set at 90 rpm for 1 hour 25 minutes at 20° C. The vaccine referred to as PER.C6®-SH-AlOH was then aliquoted aseptically at 24 ml/vial (two vials) and stored at 4° C.

PER.C6®-SH was formulated with REHYDRAPHOS® as follows: 33.85 ml medium was added to 12 ml of clarified inactivated virus bulk (pH 7.2-7.4) in a clean, sterile 100 ml bottle. Subsequently, 2.15 ml of REHYDRAPHOS® was added. The solution was manually swirled and then set on an orbital shaker set at 90 rpm for 1 hour 25 minutes at 20° C. The vaccine referred to as PER.C6®-SH-AlPh was then aliquoted aseptically at 24 ml/vial (two vials) and stored at 4° C.

PER.C6®-SH was formulated as follows, to obtain a control vaccine without adjuvant: 36 ml medium was added to 12 ml of clarified inactivated virus bulk (pH 7.2-7.4) in a clean, sterile 100 ml bottle. The solution was manually swirled and then set on an orbital shaker set at 90 rpm for 1 hour 25 minutes at 20° C. The vaccine was then aliquoted aseptically at 24 ml/vial (two vials) and stored at 4° C.

Mouse Brain-WN, PER.C6®-WN and PER.C6®-SH vaccines were formulated with Mineral Oil using methods known to persons skilled in the art of adjuvantizing vaccines. These preparations were referred to as Mouse Brain-WN-MO, PER.C6®-WN-MO and PER.C6®-SH-MO, respectively.

The study enrolled 400 geese (Anser anser, females and males, three weeks old). All animals were housed in rooms grouped according to their vaccination separate from other animals (Group size: n=20). All the rooms were fitted with mosquito-proof netting. All animals included in this study were monitored daily for behavior and general health. At day 0, prior to the administration of the primary injection, and at days 14 and 35, prior to the second injection and challenge with West Nile Virus, respectively, blood samples were collected from all animals from the jugular vein. Sera processed from blood samples were used in anti-WN-E protein ELISA assays and in plaque-reduction neutralization (PRNT) assays.

Figure 9:
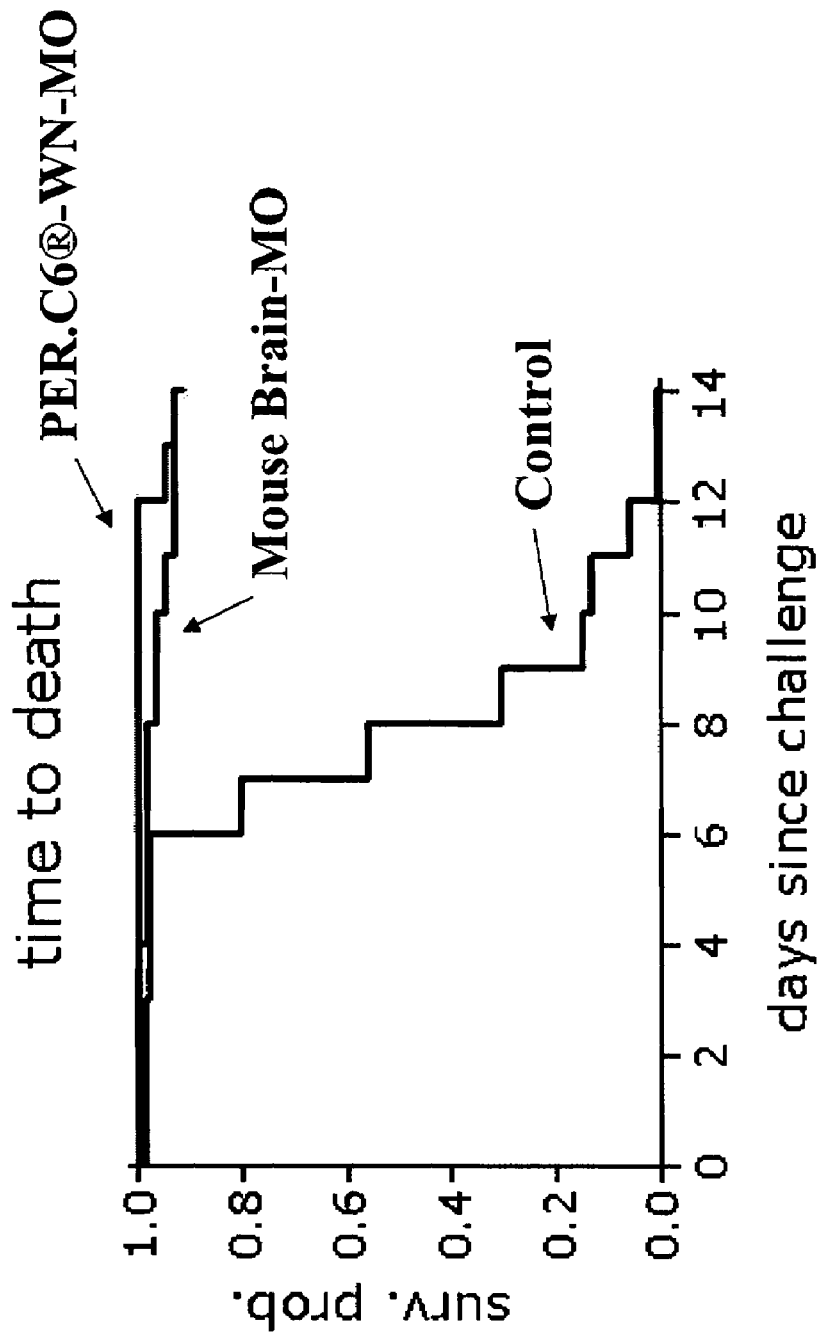
FIG. 9 is a graphical representation of part of the data shown in Table XVII for the Mouse Brain-MO and PER.C6®-WN-MO vaccines. Animals that died before challenge (two in both groups, leaving 58 animals in both groups for challenge) were not included in this figure.
Figure 10:
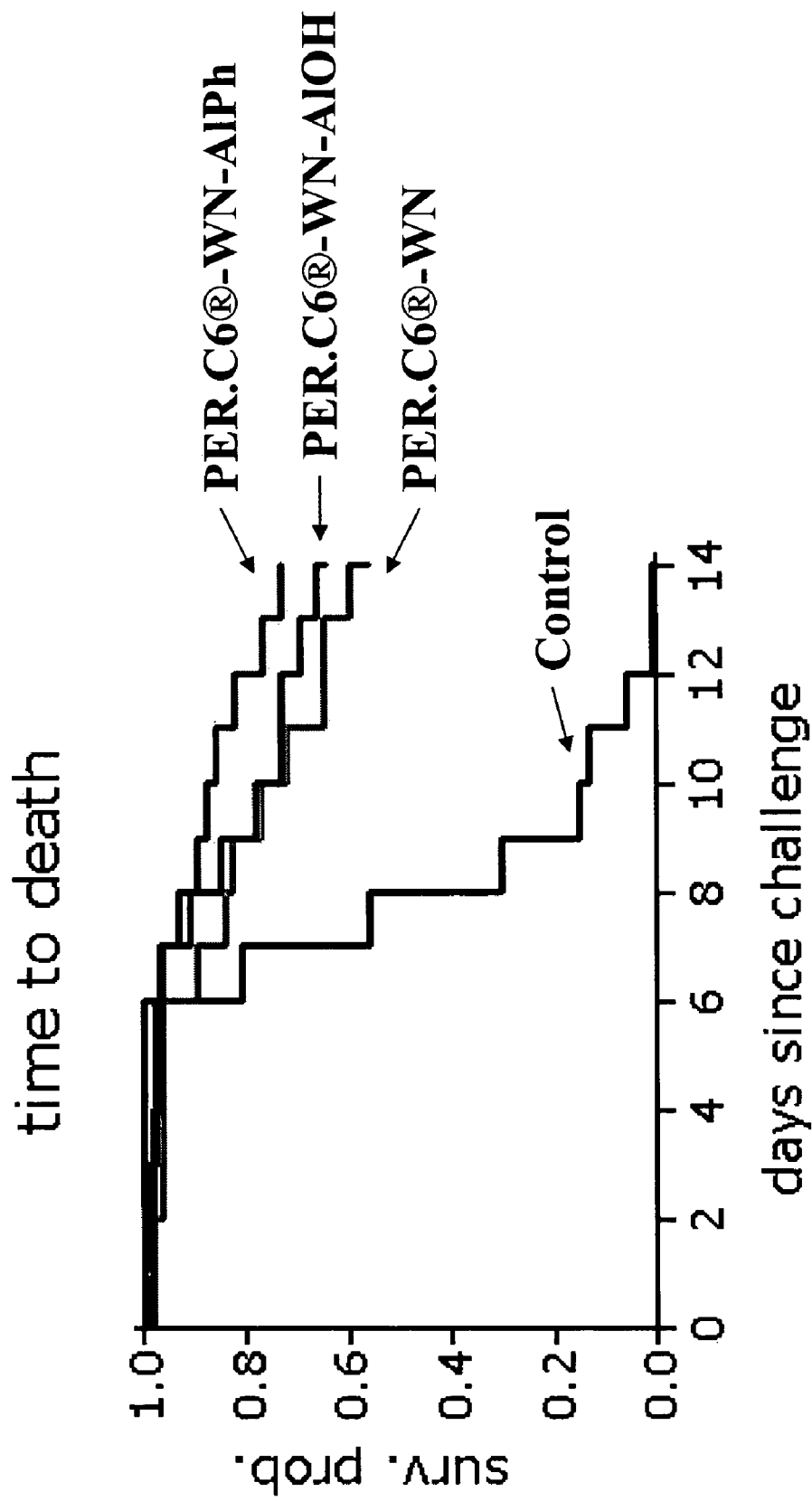
FIG. 10 is a graphical representation of part of the data shown in Table XVII for the different PER.C6®-based vaccines with or without aluminum-based adjuvants. Animals that died in these groups before challenge (one for PER.C6®-WN-AlOH leaving 59 animals; four in PER.C6®-WN-AlPh, leaving 56 animals; three in PER.C6®-WN, leaving 57 animals) were not included in this figure.

The geese were divided and treated as shown in Table XIV. Injections were performed on days 0 and 14. One ml per injection was administered subcutaneously in the neck (s.c.). On day 35 (three weeks after the second vaccination), all the animals were challenged intra-cerebrally (i.c.). The West Nile challenge virus (Goose Israel 1998) was passaged three times in VERO cells and titrated in VERO cells. A stock of virus was aliquoted and stored at −70° C. The virus was inoculated intra-cranially into the geese at a dose of $10^{2.0}$ TCID50/0.1 ml. After challenge, animals were scored for morbidity and mortality twice daily. Among the 400 geese included in the experiment, 14 geese died during the study. Two animals died in the Mouse Brain-MO group (leaving 58 animals for challenge), while in the PER.C6®-WN-MO group, two animals died before challenge. All the animals that died before challenge were included in the statistical analysis, since the risk of vaccination has to be taken into account (intention-to-treat analysis). The results are shown in Tables XV to XVIII and FIGS. 9 and 10.

Clearly, the data indicate that a West Nile Virus vaccine produced on PER.C6® raises a proper protection against a West Nile Virus challenge, which confirms the earlier findings with smaller groups of geese. It seems as if the mineral oil adjuvant works best in these veterinary vaccines using geese. The difference between the data obtained with the Mouse Brain vaccine plus mineral oil (Mouse brain-MO) and PER.C6®-based vaccine plus mineral oil (PER.C6®-WN-MO) is not significant, which indicates that (in this large group of animals) both vaccines are highly suited for use as a veterinary vaccine. The data also shows that the difference between Mouse Brain-MO and PER.C6®-WN-AlOH is significant, which means that in geese, a significantly lower number of animals are protected against disease and death when the aluminum hydroxide adjuvant is applied, as compared to the use of mineral oil. The same holds true for the aluminum phosphate adjuvant in comparison to mineral oil. However, since the number of surviving animals in the groups that received a PER.C6®-based West Nile Virus vaccine without an adjuvant is lower than in the groups with an adjuvant, this data is indicative that an adjuvant adds to the protection capacity of the vaccine.

Although these results suggest that mineral oil is the best-suited adjuvant, this cannot be extrapolated to the human situation. First, mineral oil is not suited for human use, so it will be hard to test whether these results will be reflected in the human situation, and second, humans may be more responsive towards aluminum-based adjuvants than animals such as geese. Studies toward the most suitable adjuvant for human use in combination with the PER.C6®-based West Nile Virus vaccine are to be performed. We predict that a vaccine preparation with Alum (aluminum hydroxide or aluminum phosphate) as adjuvant will be useful to protect humans against West Nile Virus infections.

Example 9

Production of West Nile Viruses on Suspension-growing PER.C6® Cells

For high volume culture of cells in vitro, it is preferred to grow the cells in dense cultures to subsequently reach the highest titers of viruses produced. For high-density cultures, it is preferred that cells grow in suspension instead of in attached settings. PER.C6® is a cell line that has proven to grow well in both settings. An experiment was performed to see whether suspension-growing PER.C6® cells could sustain the growth of West Nile Viruses and to compare these results to the production in attached settings. Example 7 already showed that different West Nile Viruses could infect PER.C6® cells and that these cells (in attached setting) were able to sustain growth to significant titers. For the suspension growth, two different available suspension culture media were used: VPRO (JRH) and APM (Gibco).

Figure 11A:
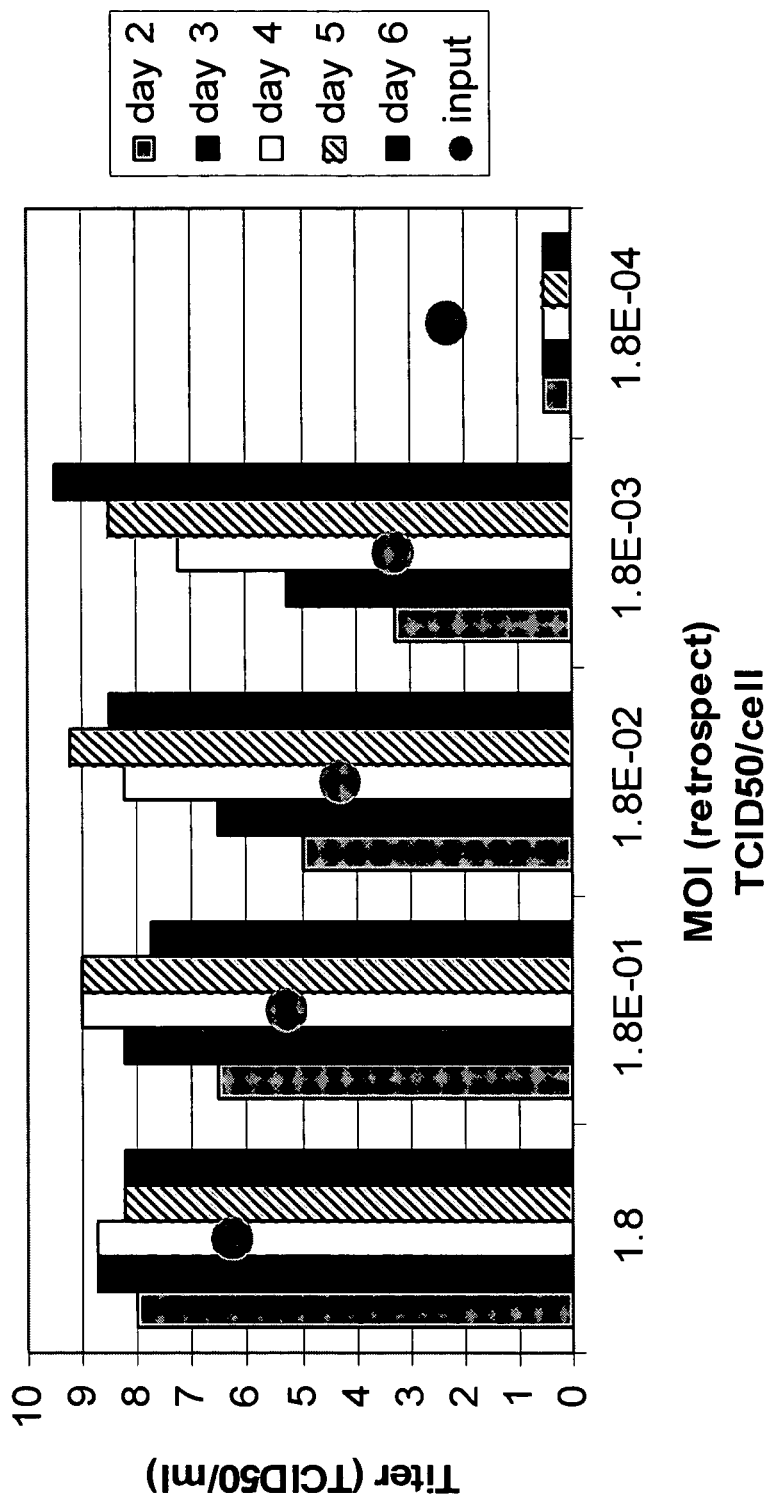
FIGS. 11A and 11B show TCID50 titers obtained with West Nile Virus derived from suspension-growing PER.C6® cells. The data depicted in the graph of FIG. 11A was obtained growing the PER.C6® cells in VPRO suspension culture media from JRH. The data depicted in the graph of FIG. 11B was obtained growing the PER.C6® cells in APM suspension culture media from Gibco. Samples were taken at days 2, 3, 4, 5, and 6 post-infection and assayed for TCID50/ml. Virus dilution is shown on the x-axis and titer is shown on the y-axis.
Figure 11B:
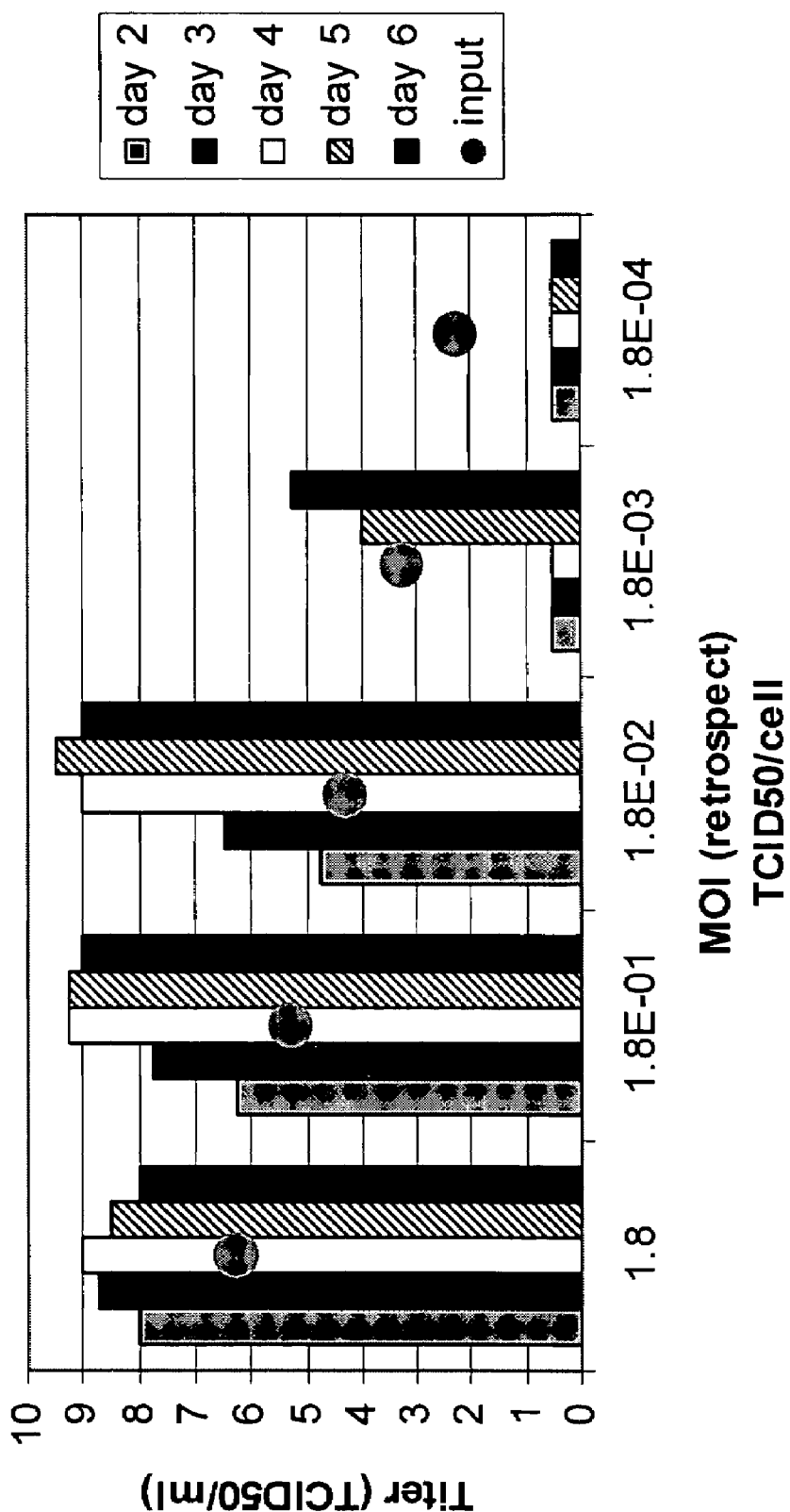

The experiment was performed as follows: 6-well plates containing $1 \times 10^6$ cells per ml were inoculated with different input virus moi. Samples were taken on day 2, 3, 4, 5 and 6 post-infection and TCID50/ml titers were determined. The results are depicted in FIG. 11A (VPRO medium) and FIG. 11B (APM medium).

The results indicate that suspension-growing PER.C6® cells are capable of sustaining growth of West Nile Virus to high titers. Thus, this indicates that PER.C6® is a proper choice for growing West Nile Viruses for obtaining large batches and thereby obtaining large amounts of vaccines for both human as well as veterinary use in a safe, clean and easy-to-handle high-throughput way.

TABLE I

Identified lineage I and II strains of West Nile Viruses (from Lanciotti et al. 2002).

| Lineage I strains | Lineage II strains |
|---|---|
| Egypt 1951 | Kenya |
| France 1965 | Uganda |
| South Africa | Senegal 1990 |
| Israel 1952 | Uganda 1937 |

TABLE I-continued

Identified lineage I and II strains of West Nile Viruses (from Lanciotti et al. 2002).

| Lineage I strains | Lineage II strains |
|---|---|
| Romania 1996 M | C. Afr. Rep 1972a |
| Kenya 1998 | C. Afr. Rep 1972b |
| Senegal 1993 | C. Afr. Rep 1983 |
| Morocco 1996 | Uganda 1959 |
| Italy 1998 | Madagascar 1988 |
| Volgograd 1999 | Madagascar 1986 |
| New York 1999 | Madagascar 1978 |
| Goose Israel 1998 | Cyprus 1968 |
| NY2000 3282 | |
| NY2000 3356 | |
| NY 1999 equine | |
| NY 1999 hum | |
| Conn 1999 | |
| Romania 1996 | |
| Romania 1996 H | |
| MD 2000 | |
| NJ 2000 | |
| Israel 1999 H | |
| C. Afr. Rep 1989 | |
| Senegal 1979 | |
| Algeria 1968 | |
| C. Afr. Rep 1967 | |
| Ivory Coast 1981 | |
| Kunjin (strains 1960, 1973, 1984b, 1991, 1984a, 1966 and 1994) | |
| India (strains 1955a, 1980, 1958, 1955b) | |

TABLE II

CPE score (in %) on PER.C6 ® cells infected with serial dilutions of West Nile Virus B956 (moi ranges from 5 to $5 \times 10^{-7}$ pfu/cell). CPE was scored 24 hours, 48 hours and 72 hours post-infection. Input virus titer was $5 \times 10^8$ pfu/ml as determined in plaque assays using Vero cells and using general methods applied in the art. CPE was not scored on the samples depicted as "nd"; these were discarded since full CPE was already detected at 48 hours post-infection.

| | | | % CPE | | |
|---|---|---|---|---|---|
| Dilution (v/v) | moi (pfu/cell) | Input virus (pfu/flask) | 24 hours post-infection | 48 hours post-infection | 72 hours post-infection |
| mock | 0 | 0 | 0 | 0 | 0 |
| $10^{-1}$ | 5 | $5 \times 10^7$ | 0 | 100 | nd |
| $10^{-2}$ | $5 \times 10^{-1}$ | $5 \times 10^6$ | 0 | 100 | nd |
| $10^{-3}$ | $5 \times 10^{-2}$ | $5 \times 10^5$ | 0 | 50 | 100 |
| $10^{-4}$ | $5 \times 10^{-3}$ | $5 \times 10^4$ | 0 | 5 | 100 |
| $10^{-5}$ | $5 \times 10^{-4}$ | $5 \times 10^3$ | 0 | 0 | 80 |
| $10^{-6}$ | $5 \times 10^{-5}$ | $5 \times 10^2$ | 0 | 0 | 50 |
| $10^{-7}$ | $5 \times 10^{-6}$ | 50 | 0 | 0 | 0 |
| $10^{-8}$ | $5 \times 10^{-7}$ | 5 | 0 | 0 | 0 |

TABLE III

West Nile Virus titers as determined by real-time RT-TAQMAN ® PCR. Titers are given in pfu/ml (right columns depicted as 24 hours, 48 hours and 72 hours post-infection).

| Dilution | moi pfu/cell | Input virus pfu/flask | 24 hours post-infection | 48 hours post-infection | 72 hours post-infection |
|---|---|---|---|---|---|
| $10^{-1}$ | 5 | $5 \times 10^7$ | $3.6 \times 10^7$ | $5.9 \times 10^7$ | nd |
| $10^{-2}$ | $5 \times 10^{-1}$ | $5 \times 10^6$ | $6.5 \times 10^6$ | $2.7 \times 10^7$ | nd |
| $10^{-3}$ | $5 \times 10^{-2}$ | $5 \times 10^5$ | $1.9 \times 10^6$ | $6.1 \times 10^7$ | nd |
| $10^{-4}$ | $5 \times 10^{-3}$ | $5 \times 10^4$ | $2.5 \times 10^5$ | $1.9 \times 10^7$ | $1.0 \times 10^9$ |
| $10^{-5}$ | $5 \times 10^{-4}$ | $5 \times 10^3$ | $2.2 \times 10^4$ | $5.7 \times 10^6$ | $4.3 \times 10^8$ |
| $10^{-6}$ | $5 \times 10^{-5}$ | $5 \times 10^2$ | $5.6 \times 10^3$ | $7.1 \times 10^5$ | $1.5 \times 10^8$ |
| $10^{-7}$ | $5 \times 10^{-6}$ | 50 | $3.4 \times 10^3$ | $7.9 \times 10^4$ | $9.8 \times 10^7$ |
| $10^{-8}$ | $5 \times 10^{-7}$ | 5 | $5.5 \times 10^3$ | $4.2 \times 10^3$ | $1.2 \times 10^6$ |

TABLE IV

Vaccination scheme using PER.C6 ®-based West Nile vaccine and a Mouse brain-produced West Nile vaccine in two-week-old geese.

| Group (n=) | Material | Volume | Vaccination | Adjuvant |
|---|---|---|---|---|
| PART A | | | | |
| 1. 20 | WN vaccine PER.C6 ® | 0.25 ml | Day 0 Day 14 | None |
| 2. 22 | WN vaccine PER.C6 ® | 0.5 ml | Day 0 Day 14 | None |
| 3. 23 | WN vaccine PER.C6 ® | 1 ml | Day 0 Day 14 | None |
| PART B | | | | |
| 1. 25 | WN vaccine PER.C6 ® | 0.25 ml | Day 0 Day 14 | Mineral oil |
| 2. 25 | WN vaccine PER.C6 ® | 0.5 ml | Day 0 Day 14 | Mineral oil |
| 3. 28 | WN vaccine PER.C6 ® | 1.0 ml | Day 0 Day 14 | Mineral oil |
| PART C | | | | |
| 1. 19 | Mouse brain vaccine | 0.25 ml | Day 0 Day 14 | Mineral oil |
| 2. 20 | Mouse brain vaccine | 0.5 ml | Day 0 Day 14 | Mineral oil |
| 3. 18 | Mouse brain vaccine | 1.0 ml | Day 0 Day 14 | Mineral oil |
| 4. 13 | No Vaccine | | | |

TABLE V

Results of the experiment showing the percentage of geese surviving (and being disease free) upon vaccination with whole-inactivated West Nile Viruses (WNV) produced in tissue culture using PER.C6 ® cells or using mouse brains (MB) and challenged with West Nile Virus strain Goose Israel 1998. Certain West Nile Virus vaccines held Mineral Oil as an adjuvant, as indicated. The volume of the vaccine as described in the description is also indicated. N represents the number of animals per group. The control group of 13 animals did not receive any vaccine and all died upon challenge.

| Vaccine | Volume | Adjuvant | N | Disease/ Death | Disease free/ survival |
|---|---|---|---|---|---|
| WNV PER.C6 ® | 1.0 ml | None | 23 | 15 | 34.8% |
| WNV PER.C6 ® | 0.5 ml | None | 22 | 10 | 54.6% |
| WNV PER.C6 ® | 0.25 ml | None | 20 | 11 | 45.0% |
| WNV PER.C6 ® | 1.0 ml | Mineral Oil | 28 | 2 | 92.9% |
| WNV PER.C6 ® | 0.5 ml | Mineral Oil | 25 | 3 | 88.0% |
| WNV PER.C6 ® | 0.25 ml | Mineral Oil | 25 | 3 | 88.0% |
| WNV MB | 1.0 ml | Mineral Oil | 18 | 1 | 94.4% |
| WNV MB | 0.5 ml | Mineral Oil | 20 | 1 | 95.0% |
| WNV MB | 0.25 ml | Mineral Oil | 19 | 2 | 89.5% |
| Control | — | — | 13 | 13 | 0% |

TABLE VI

The results of Table V taken together for the geese groups that received the Mouse Brain-derived vaccine and the PER.C6 ®-derived vaccine (all with Mineral Oil as adjuvant) as compared to the control group that did not receive vaccination.

| Vaccine | Adjuvant | N | Disease/Death | Disease free/survival |
|---|---|---|---|---|
| WNV PER.C6 ® | Mineral Oil | 78 | 8 | 89.7% |
| WNV MB | Mineral Oil | 57 | 4 | 93.0% |
| Control | — | 13 | 13 | 0% |

TABLE VII

Selection of Lineage I and II West Nile Virus strains used in a cross-protection assay in geese. Viruses of the different strains were produced in PER.C6 ®. They are purified, inactivated, mixed with adjuvant and used for a protection against a challenge with live Goose Israel 1998 and New York 1999 West Nile Viruses. The right two columns give the inoculation $LD_{50}$ in pfu for each of the strains as it is known from the art with respect to neuroinvasion upon intra-peritoneal (i.p.) administration or with respect to neurovirulence upon intra-cranial administration.

| Lineage | Strain | i.p. | i.c. |
|---|---|---|---|
| I | Goose Israel 1998 (Isr98) | n.d. | 0.1 |
| I | New York 1999 (USA99b) | 0.5 | 0.1 |
| I | Kunjin 1960 (Aus60) | >10,000 | n.d. |
| I | Kunjin 1991 (Aus91) | >10,000 | 3.2 |
| II | Cyprus 1968 (Cyp68) | >10,000 | 0.5 |
| II | Madagascar 1978 (Mad78) | >10,000 | n.d. |

TABLE VIII

CPE scores after infection of PER.C6 ® cells with West Nile Virus New York 1999 (NY99 isolated from a Snowy Owl, The Bronx Zoo, New York)

| USA99b dilutions | day 2 | day 3 | day 4 | day 5 | day 6 |
|---|---|---|---|---|---|
| $10^{-3}$ | + (<1%) | + (75%) | full cpe | na | na |
| $10^{-4}$ | — | + (25%) | + (75%) | full cpe | na |
| $10^{-5}$ | — | + (1%) | + (1%) | + (10%) | + (75%) |
| $10^{-6}$ | — | — | + (<1%) | + (<1%) | + (25-50%) |
| $10^{-7}$ | — | — | + (<1%) | + (<1%) | + (5%) |
| $10^{-8}$ | — | — | — | — | — |

TABLE IX

CPE scores after infection of PER.C6 ® cells with West Nile Virus Aus91 (strain Kunjin 1991 [K 6453], isolated in Australia from *Culex annulirostris* mosquitoes in 1991)

| AUS91 dilutions | day 2 | day 3 | day 4 | day 5 | day 6 |
|---|---|---|---|---|---|
| $10^{-3}$ | — | + (1%) | + (1-5%) | + (10%) | + (1-5%) |
| $10^{-4}$ | — | — | + (<1%) | + (1%) | + (1%) |
| $10^{-5}$ | — | — | — | — | — |
| $10^{-6}$ | — | — | — | — | — |
| $10^{-7}$ | — | — | — | — | — |
| $10^{-8}$ | — | — | — | — | — |

TABLE X

CPE scores after infection of PER.C6 ® cells with West Nile Virus Mad78 (strain Madagascar 1998)

| MAD78 dilutions | day 2 | day 3 | day 4 | day 5 | day 6 |
|---|---|---|---|---|---|
| $10^{-3}$ | — | — | — | + (1%) | + (1%) |
| $10^{-4}$ | — | — | — | — | + (<1%) |
| $10^{-5}$ | — | — | — | — | — |
| $10^{-6}$ | — | — | — | — | — |
| $10^{-7}$ | — | — | — | — | — |
| $10^{-8}$ | — | — | — | — | — |

TABLE XI

CPE scores after infection of PER.C6 ® cells with West Nile Virus Aus60 (strain Kunjin 1960 [MRM 16], isolated in Australia from *Culex annulirostris* mosquitoes in 1960)

| AUS60 dilutions | day 2 | day 3 | day 4 | day 5 | day 6 |
|---|---|---|---|---|---|
| $10^{-3}$ | — | — | + (25%) | + (50-75%) | + (75%) |
| $10^{-4}$ | — | — | + (1-5%) | + (1-5%) | + (10%) |
| $10^{-5}$ | — | — | — | + (<1%) | + (1%) |
| $10^{-6}$ | — | — | — | + (<1%) | — |
| $10^{-7}$ | — | — | — | — | — |
| $10^{-8}$ | — | — | — | — | — |

TABLE XII

CPE scores after infection of PER.C6 ® cells with West Nile Virus Cyp68 (strain Cyprus 1968)

| CYP68 dilutions | day 2 | day 3 | day 4 | day 5 | day 6 |
|---|---|---|---|---|---|
| $10^{-3}$ | — | + (1%) | + (1%) | + (10%) | + (25%) |
| $10^{-4}$ | — | — | — | + (1%) | + (1%) |
| $10^{-5}$ | — | — | — | — | — |
| $10^{-6}$ | — | — | — | — | — |
| $10^{-7}$ | — | — | — | — | — |
| $10^{-8}$ | — | — | — | — | — |

TABLE XIII

CPE scores after infection of PER.C6 ® cells with West Nile Virus Isr98 (strain Goose Israel 1998)

| ISR98 dilutions | day 2 | day 3 | day 4 | day 5 | day 6 |
|---|---|---|---|---|---|
| $10^{-3}$ | + (<1%) | + (50%) | full cpe | na | na |
| $10^{-4}$ | — | + (25%) | + (75%) | full cpe | na |
| $10^{-5}$ | — | + (1%) | + (1-5%) | + (50-75%) | full cpe |
| $10^{-6}$ | — | + (<1%) | + (<1%) | + (25%) | + (50%) |
| $10^{-7}$ | — | — | — | — | + (<1%) |
| $10^{-8}$ | — | — | — | — | — |

TABLE XIV

Vaccination scheme of geese using West Nile Virus vaccines comprising different adjuvant compounds.

| Group size | Material | Volume | Injections | Adjuvant |
|---|---|---|---|---|
| 3 × 20 | Mouse Brain WN-MO | 1 ml | Day 0<br>Day 14 | Mineral oil |
| 3 × 20 | PER.C6 ®-WN-MO | 1 ml | Day 0<br>Day 14 | Mineral oil |

TABLE XIV-continued

Vaccination scheme of geese using West Nile Virus vaccines comprising different adjuvant compounds.

| Group size | Material | Volume | Injections | Adjuvant |
|---|---|---|---|---|
| 3 × 20 | PER.C6®-WN-AlOH | 1 ml | Day 0<br>Day 14 | Aluminum hydroxide<br>REHYDRAGEL® |
| 3 × 20 | PER.C6®-WN-AlPh | 1 ml | Day 0<br>Day 14 | Aluminum phosphate<br>REHYDRAPHOS® |
| 3 × 20 | PER.C6®-WN | 1 ml | Day 0<br>Day 14 | None |
| 20 | PER.C6®-SH | 1 ml | Day 0<br>Day 14 | None |
| 20 | PER.C6®-SH-AlOH | 1 ml | Day 0<br>Day 14 | Aluminum hydroxide<br>REHYDRAGEL® |
| 20 | PER.C6®-SH-Alph | 1 ml | Day 0<br>Day 14 | Aluminum phosphate<br>REHYDRAPHOS® |
| 20 | PER.C6®-SH-MO | 1 ml | Day 0<br>Day 14 | Mineral oil |
| 20 | PBS | 1 ml | Day 0<br>Day 14 | |

TABLE XV

Analysis with death taken as endpoint, intention to treat (safety and efficacy).

| | N | Survival | Survival Prob | 95% CI |
|---|---|---|---|---|
| Mouse Brain MO | 60 | 54 | 90.0% | 79.9-95.0% |
| PER.C6® WN MO | 60 | 53 | 88.3% | 77.8-94.2% |
| PER.C6® WN AlOH | 60 | 38 | 63.3% | 50.7-74.4% |
| PER.C6® WN AlPh | 60 | 41 | 68.3% | 55.8-78.7% |
| PER.C6® WN | 60 | 32 | 53.3% | 40.9-65.4% |
| PER.C6® SH | 20 | 0 | 0 | 0-16.1% |
| PER.C6® SH AlOH | 20 | 0 | 0 | 0-16.1% |
| PER.C6® SH AlPh | 20 | 0 | 0 | 0-16.1% |
| PER.C6® MO | 20 | 1 | 5.0% | 0.9-23.6% |
| PBS | 20 | 0 | 0 | 0-16.1% |

N = number of animals;
CI = Confidentiality Interval

Risk difference between:
Mouse Brain-MO and PER.C6®-WN-MO:
1.7% (95% CI −9.5-12.8) not significant
Mouse Brain-MO and PER.C6®-WN-AlOH:
26.7% (95% CI 12.3-41.0) significant

TABLE XVI

Analysis with death or diseased taken as endpoint (disease-free survival)

| | N | df Survival | df Survival Prob | 95% CI |
|---|---|---|---|---|
| Mouse Brain MO | 60 | 54 | 90.0% | 79.9-95.0% |
| PER.C6® WN MO | 60 | 53 | 88.3% | 77.8-94.2% |
| *PER.C6® WN AlOH* | *60* | *31* | *51.7%* | *39.3-63.8%* |
| *PER.C6® WN AlPh* | *60* | *32* | *53.3%* | *40.9-65.4%* |
| *PER.C6® WN* | *60* | *25* | *41.7%* | *30.1-54.3%* |
| PER.C6® SH | 20 | 0 | 0 | 0-16.1% |
| PER.C6® SH AlOH | 20 | 0 | 0 | 0-16.1% |
| PER.C6® SH AlPh | 20 | 0 | 0 | 0-16.1% |
| PER.C6® MO | 20 | 1 | 5.0% | 0.9-23.6% |
| PBS | 20 | 0 | 0 | 0-16.1% |

Note:
Numbers in *italic* indicate differences with table XV.
N = number of animals;
CI = Confidentiality Interval Risk difference between:
Mouse Brain-MO and PER.C6®-WN-MO:
1.7 (95% CI −9.5-12.8%) not significant
Mouse Brain-MO and PER.C6®-WN-AlOH:
38.3 (95% CI 23.6-53.1%) significant

TABLE XVII

Analysis with death taken as endpoint among geese that were challenged with WN (to estimate true efficacy)

| | N | Survival | Survival Prob | 95% CI |
|---|---|---|---|---|
| Mouse Brain MO | 58 | 54 | 93.1 | 83.6-97.3% |
| PER.C6® WN MO | 58 | 53 | 91.4 | 81.4-96.3% |
| PER.C6® WN AlOH | 59 | 38 | 64.4 | 51.7-75.4% |
| PER.C6® WN AlPh | 56 | 41 | 73.2 | 60.4-83.0% |
| PER.C6® WN | 57 | 32 | 56.1 | 43.3-68.2% |
| PER.C6® SH | 19 | 0 | 0 | 0-16.8% |
| PER.C6® SH AlOH | 20 | 0 | 0 | 0-16.1% |
| PER.C6® SH AlPh | 20 | 0 | 0 | 0-16.1% |
| PER.C6® MO | 20 | 1 | 5.0 | 0.9-23.6% |
| PBS | 19 | 0 | 0 | 0-16.8% |

N = number of animals;
CI = Confidentiality Interval

Risk difference between:
Mouse Brain-MO and PER.C6®-WN-MO:
1.7 (95% CI −8.0-11.5) not significant
Mouse Brain-MO and PER.C6®-WN-AlOH:
28.7 (95% CI 14.9-42.6) significant

TABLE XVIII

Analysis with endpoint "death before challenge" to study the safety of vaccination

| | N | Survival | Survival Prob | 95% CI |
|---|---|---|---|---|
| Mouse Brain MO | 60 | 58 | 96.7 | 88.6-99.1% |
| PER.C6® WN MO | 60 | 58 | 96.7 | 88.6-99.1% |
| PER.C6® WN AlOH | 60 | 59 | 98.3 | 91.1-99.7% |
| PER.C6® WN AlPh | 60 | 56 | 93.3 | 84.1-97.4% |
| PER.C6® WN | 60 | 57 | 95.0 | 86.3-98.3% |
| PER.C6® SH | 20 | 19 | 95 | 76.4-99.1% |
| PER.C6® SH AlOH | 20 | 20 | 100 | 83.9-100% |
| PER.C6® SH AlPh | 20 | 20 | 100 | 83.9-100% |
| PER.C6® MO | 20 | 20 | 100 | 83.9-100% |
| PBS | 20 | 19 | 95 | 76.4-99.1% |

N = number of animals;
CI = Confidentiality Interval

Risk difference between:
Mouse Brain-MO and PER.C6®-WN-MO:
0 (95% CI −6.4-6.4) not significant
Mouse Brain-MO and PER.C6®-WN-AlOH:
1.7 (95% CI −3.9-7.3) not significant

REFERENCES

Anderson J. F., Andreadis T. G., Vossbrinck C. R., Tirrell S., Wakem E. M., French R. A., Garmendia A. E. and Van Kruiningen H. J. (1999) Isolation of West Nile Virus from mosquitoes, crows, and a Cooper's hawk in Connecticut. *Science* 286:2331-2333.

Arroyo J., Miller C. A., Catalan J. and Monath T. P. (2001) Yellow fever vector live-virus vaccines: West Nile Virus vaccine development. *Trends Mol. Med.* 7:350-354.

Bin H., Grossman Z., Pokamunski S., Malkinson M., Weiss L., Duvdevani P., Banet C., Weisman Y., Annis E., Gandaku D., Yahalom V., Hindyieh M., Shulman L. and Mendelson E. (2001) West Nile fever in Israel 1999-2000: from geese to humans. *Ann. N.Y. Acad. Sci.* 951:127-142.

Brinton M. A. (2002) The molecular biology of West Nile Virus: A new invader of the Western Hemisphere. *Annu. Rev. Microbiol.* 56:371-402.

Campbell G. L., Marfin A. A., Lanciotti R. S. and Gubler D. J. (2002) West Nile Virus. *Lancet Infect. Dis.* 2:519-529.

Chambers T. J., Hahn C. S., Galler R. and Rice C. M. (1990) Flavivirus genome organization, expression, and replication. *Annu. Rev. Microbiol.* 44:649-688.

Chang G. J., Davis B. S., Hunt A. R., Holmes D. A. and Kuno G. (2001) Flavivirus DNA vaccines: current status and potential. *Ann. N.Y. Acad. Sci.* 951:272-285.

Dunster L. M., Gibson C. A., Stephenson J. R., Minor P. D. and Barrett A. D. (1990) Attenuation of virulence of flaviviruses following passage in HeLa cells. *J. Gen. Virol.* 71:601-607.

Hadfield T. L., Turell M., Dempsey M. P., David J. and Park E. J. (2001) Detection of West Nile Virus in mosquitoes by RT-PCR. *Mol. Cell Probes* 15:147-150.

Hubalek Z. and Halouzka J. (1999) West Nile fever—A reemerging mosquito-borne viral disease in Europe. *Emerg. Infect. Dis.* 5:643-650.

Jia X. Y., Briese T., Jordan I., Rambaut A., Chi H. C., Mackenzie J. S., Hall R. A., Scherret J. and Lipkin W. I. (1999) Genetic analysis of West Nile New York 1999 encephalitis virus. *Lancet* 354:1971-1972.

Kurane I., Janus J. and Ennis F. A. (1992) Dengue virus infection of human skin fibroblasts in vitro production of IFN-beta, IL-6 and GM-CSF. *Arch. Virol.* 124:21-30.

Lanciotti R. S., Roehrig J. T., Deubel V. et al. (1999) Origin of the West Nile Virus responsible for an outbreak of encephalitis in the northeastern United States. *Science* 286:2333-2337.

Lanciotti R. S., Kerst A. J., Nasci R. S. et al. (2000) Rapid detection of West Nile Virus from human clinical specimens, field-collected mosquitoes, and avian samples by a TAQMAN® reverse transcriptase-PCR assay. *J. Clin. Microbiol.* 38:4066-4071.

Lanciotti R. S., Ebel G. D., Deubel V. et al. (2002) Complete genome sequences and phylogenetic analysis of West Nile Virus strains isolated from the United States, Europe and the Middle East. *Virology* 298:96-105.

Malkinson M., Banet C., Mahany S. et al. (1998) Virus encephalomyelitis of geese: some properties of the viral isolate. *Isr. J. Vet. Med.* 53:44.

Malkinson M., Banet C., Khinich Y., Samina I., Pokamunski S. and Weisman Y. (2001) Use of live and inactivated vaccines in the control of West Nile fever in domestic geese. *Ann. N. Y. Acad. Sci.* 951:255-261.

Monath T. P. (2001) Prospects for development of a vaccine against the West Nile Virus. *Ann. N.Y. Acad. Sci.* 951:1-12.

Smithburn K. C., Hughes T. P., Burke A. V. and Paul J. H. (1940) A neurotropic virus isolated from the blood of a native of Uganda. *Am. J. Trop. Med. Hyg.* 20:471-492.

Wang T., Anderson J. F., Magnarelli L. A., Wong S. J., Koski R. A. and Fikrig E. (2001) Immunization of mice against West Nile Virus with recombinant envelope protein. *J. Immunol.* 167:5273-5277.

Wengler G., Wengler G., Nowak T. and Castle E. (1990) Description of a procedure which allows isolation of viral non-structural proteins from BHK vertebrate cells infected with the West Nile flavivirus in a state which allows their direct chemical characterization. *Virology* 177:795-801.

Yamshchikov V. F., Wengler G., Perelygin A. A., Brinton M. A. and Compans R. W. (2001) An infectious clone of the West Nile Flavivirus. *Virology* 281:294-304.

What is claimed is:

1. A method of producing a West Nile Virus, said method comprising:

infecting a cell with West Nile Virus, wherein the cell comprises an E1 region of an adenovirus integrated into the cell's chromosomal genome;

culturing the cell in a suitable medium under conditions that allow for the production of the West Nile Virus; and producing West Nile Virus.

2. The method according to claim 1, wherein the cell is a non-tumorous human cell.

3. The method according to claim 1, wherein the cell is a retinoblast.

4. The method according to claim 1, wherein the cell is an embryonic cell.

5. The method according to claim 1, wherein the cell is an embryonic retinoblast.

6. The method according to claim 1, wherein the cell is a PER.C6® cell.

7. The method according to claim 1, wherein the cell is a kidney cell or an ammocyte.

8. The method according to claim 1, wherein said West Nile Virus is selected from the group consisting of lineage II strain West Nile B956, lineage II strain Madagascar 1978, lineage II strain Cyprus 1968, lineage I strain Kunjin 1960, lineage I strain Kunjin 1991, lineage I strain Goose Israel 1998, and lineage I strain New York 1999.

9. The method according to claim 1, wherein said West Nile Virus is a lineage II strain selected from the group consisting of Kenya, Uganda, Senegal 1990, Uganda 1937, Uganda 1959, Central African Republic 1972a, Central African Republic 1972b, Central African Republic 1983, Madagascar 1986 and Madagascar 1988.

10. The method according to claim 1, wherein said cell is infected with a West Nile Virus at a multiplicity of infection ranging from about 5 to about $5 \times 10^{-7}$ plaque forming units per cell.

11. The method according to claim 1, wherein culturing the cell comprises culturing the cell in serum-free medium.

12. The method according to claim 1, wherein culturing the cell comprises culturing the cell in a suspension culture.

13. The method according to claim 1, wherein the cell comprises a temperature-sensitive E2A gene.

14. The method according to claim 1, further comprising inactivating the produced West Nile Virus.

15. The method according to claim 14, further comprising:

harvesting the produced West Nile Virus, wherein harvesting comprises purifying the West Nile Virus particles.

16. The method according to claim 1, further comprising:

disrupting the produced West Nile Virus; and purifying one or more anti genie components of said West Nile Virus.

17. The method according to claim 14, wherein said produced West Nile Virus is inactivated with formaldehyde.

* * * * *

UNITED STATES PATENT AND TRADEMARK OFFICE
CERTIFICATE OF CORRECTION

PATENT NO.         : 7,425,437 B2                                   Page 1 of 1
APPLICATION NO.    : 11/110517
DATED              : September 16, 2008
INVENTOR(S)        : UytdeHaag et al.

It is certified that error appears in the above-identified patent and that said Letters Patent is hereby corrected as shown below:

On the title page:
In ITEM [63] Related U.S.
Application Data:                change "PCT/EP2003/05080," to --PCT/EP2003/050806,--

In the claims:
CLAIM 7,   COLUMN 27,   LINE 34,     change "ammocyte." to --amniocyte.--
CLAIM 16,  COLUMN 28,   LINE 35,     change "anti genie" to --antigenic--

Signed and Sealed this
Twenty-fourth Day of December, 2013

Margaret A. Focarino
*Commissioner for Patents of the United States Patent and Trademark Office*

```
                         SEQUENCE LISTING

<160> NUMBER OF SEQ ID NOS: 3

<210> SEQ ID NO 1
<211> LENGTH: 21
<212> TYPE: DNA
<213> ORGANISM: Artificial
<220> FEATURE:
<223> OTHER INFORMATION: Synthetic oligonucleotide WNV 1

<400> SEQUENCE: 1
ccaccggawg ttgagtagac g                                          21

<210> SEQ ID NO 2
<211> LENGTH: 20
<212> TYPE: DNA
<213> ORGANISM: Artificial
<220> FEATURE:
<223> OTHER INFORMATION: Synthetic oligonucleotide WNV 2

<400> SEQUENCE: 2
tttgktcacc cagtcctcct                                            20

<210> SEQ ID NO 3
<211> LENGTH: 20
<212> TYPE: DNA
<213> ORGANISM: Artificial
<220> FEATURE:
<223> OTHER INFORMATION: Synthetic oligonucleotide VIC labelled probe
<220> FEATURE:
<221> NAME/KEY: misc_feature
<222> LOCATION: (1)..(1)
<223> OTHER INFORMATION: VIC label attached
```

```
<220> FEATURE:
<221> NAME/KEY: misc_feature
<222> LOCATION: (20)..(20)
<223> OTHER INFORMATION: TAMRA label attached

<400> SEQUENCE: 3
tgctgcctgc grctcaaccc                                              20
```